(12) United States Patent
Olson et al.

(10) Patent No.: US 8,940,712 B2
(45) Date of Patent: Jan. 27, 2015

(54) MICRO-RNA FAMILY THAT MODULATES FIBROSIS AND USES THEREOF

(71) Applicant: The Board of Regents, The University of Texas System, Austin, TX (US)

(72) Inventors: Eric N. Olson, Dallas, TX (US); Eva van Rooij, Utrecht (NL)

(73) Assignee: The Board of Regents, The University of Texas System, Austin, TX (US)

( * ) Notice: Subject to any disclaimer, the term of this patent is extended or adjusted under 35 U.S.C. 154(b) by 1 day.

(21) Appl. No.: 13/840,823

(22) Filed: Mar. 15, 2013

(65) Prior Publication Data

US 2013/0195891 A1    Aug. 1, 2013

Related U.S. Application Data

(63) Continuation of application No. 12/671,445, filed as application No. PCT/US2008/071839 on Jul. 31, 2008, now Pat. No. 8,440,636.

(60) Provisional application No. 61/047,014, filed on Apr. 22, 2008, provisional application No. 60/980,303, filed on Oct. 16, 2007, provisional application No. 60/952,917, filed on Jul. 31, 2007.

(51) Int. Cl.

| | |
|---|---|
| *C12N 15/11* | (2006.01) |
| *A61K 31/713* | (2006.01) |
| *A01K 67/027* | (2006.01) |
| *A61K 38/22* | (2006.01) |
| *C12N 9/16* | (2006.01) |
| *C12N 15/113* | (2010.01) |
| *C12N 15/85* | (2006.01) |
| *A61K 31/7105* | (2006.01) |
| *A61K 31/712* | (2006.01) |
| *A61K 31/7125* | (2006.01) |
| *A61K 39/395* | (2006.01) |
| *A61K 45/06* | (2006.01) |
| *A61K 31/07* | (2006.01) |
| *A61K 31/355* | (2006.01) |
| *A61K 31/375* | (2006.01) |

(52) U.S. Cl.
CPC ........... *A61K 31/713* (2013.01); *A01K 67/0276* (2013.01); *A61K 38/2242* (2013.01); *C12N 9/16* (2013.01); *C12N 15/113* (2013.01); *C12N 15/8509* (2013.01); *A61K 31/7105* (2013.01); *A61K 31/712* (2013.01); *A61K 31/7125* (2013.01); *A61K 39/3955* (2013.01); *A61K 45/06* (2013.01); *A61K 31/07* (2013.01); *A61K 31/355* (2013.01); *A61K 31/375* (2013.01); *A01K 2207/30* (2013.01); *A01K 2217/052* (2013.01); *A01K 2217/075* (2013.01); *A01K 2217/15* (2013.01); *A01K 2217/206* (2013.01); *A01K 2227/105* (2013.01); *A01K 2267/0375* (2013.01); *C12N 2310/113* (2013.01); *C12N 2310/141* (2013.01); *C12N 2310/315* (2013.01); *C12N 2310/321* (2013.01); *C12N 2310/346* (2013.01); *C12N 2310/3515* (2013.01); *C12N 2320/31* (2013.01); *C12N 2330/10* (2013.01)
USPC ...................................................... 514/44 A

(58) Field of Classification Search
USPC ........................................................ 514/44 A
See application file for complete search history.

(56) References Cited

U.S. PATENT DOCUMENTS

| | | |
|---|---|---|
| 7,232,806 B2 | 6/2007 | Tuschl et al. |
| 7,674,617 B2 | 3/2010 | Kim et al. |
| 2005/0059005 A1 | 3/2005 | Tuschl et al. |
| 2005/0222399 A1 | 10/2005 | Bentwich |
| 2005/0261218 A1 | 11/2005 | Esau et al. |
| 2006/0019286 A1 | 1/2006 | Horvitz et al. |
| 2006/0105360 A1 | 5/2006 | Croce et al. |
| 2006/0185027 A1 | 8/2006 | Bartel et al. |
| 2006/0247193 A1 | 11/2006 | Taira et al. |
| 2007/0087335 A1 | 4/2007 | Brahmachari et al. |
| 2007/0092882 A1 | 4/2007 | Wang et al. |
| 2008/0050722 A1 | 2/2008 | Kim et al. |
| 2008/0176766 A1 | 7/2008 | Brown et al. |
| 2009/0053718 A1 | 2/2009 | Naguibneva et al. |
| 2009/0092980 A1 | 4/2009 | Arenz et al. |
| 2009/0143326 A1 | 6/2009 | Obad et al. |
| 2009/0281167 A1 | 11/2009 | Shen et al. |

(Continued)

FOREIGN PATENT DOCUMENTS

| | | |
|---|---|---|
| EP | 1440981 A2 | 7/2004 |
| EP | 1627925 A1 | 2/2006 |

(Continued)

OTHER PUBLICATIONS

Cheng et al., "MicroRNAs Are Aberrantly Expressed in Hypertrophic Heart," Am. J. Pathol. 170(6):1831-1840 (2007).

(Continued)

*Primary Examiner* — J. E. Angell
(74) *Attorney, Agent, or Firm* — Cooley LLP

(57) ABSTRACT

The present invention relates to the identification of a microRNA family, designated miR-29a-c, that is a key regulator of fibrosis in cardiac tissue. The inventors show that members of the miR-29 family are down-regulated in the heart tissue in response to stress, and are up-regulated in heart tissue of mice that are resistant to both stress and fibrosis. Also provided are methods of modulating expression and activity of the miR-29 family of miRNAs as a treatment for fibrotic disease, including cardiac hypertrophy, skeletal muscle fibrosis other fibrosis related diseases and collagen loss-related disease.

16 Claims, 25 Drawing Sheets

(56) References Cited

U.S. PATENT DOCUMENTS

| | | |
|---|---|---|
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0293148 A1 | 11/2009 | Ren et al. |
| 2009/0317369 A1 | 12/2009 | Hosoda et al. |
| 2009/0326049 A1 | 12/2009 | Aristarkhov et al. |
| 2010/0029003 A1 | 2/2010 | Bartel et al. |
| 2010/0087512 A1 | 4/2010 | Tuschl et al. |
| 2010/0087513 A1 | 4/2010 | Tuschl et al. |
| 2010/0093837 A1 | 4/2010 | Tuschl et al. |
| 2010/0099748 A1 | 4/2010 | Tuschl et al. |
| 2010/0113561 A1 | 5/2010 | Tuschl et al. |

FOREIGN PATENT DOCUMENTS

| | | |
|---|---|---|
| EP | 1777301 A2 | 4/2007 |
| EP | 1959012 A2 | 8/2008 |
| EP | 2113567 A1 | 11/2009 |
| JP | 2006-519008 | 8/2006 |
| JP | 2006-292367 | 10/2006 |
| WO | WO 03/029459 A2 | 4/2003 |
| WO | WO 2004/076622 A2 | 9/2004 |
| WO | WO 2005/013901 A2 | 2/2005 |
| WO | WO 2005/017145 A1 | 2/2005 |
| WO | WO 2005/040419 A1 | 5/2005 |
| WO | WO 2005/047505 A2 | 5/2005 |
| WO | WO 2005/056797 A1 | 6/2005 |
| WO | WO 2005/118806 A2 | 12/2005 |
| WO | WO 2006/033020 A2 | 3/2006 |
| WO | WO 2006/033928 A2 | 3/2006 |
| WO | WO 2006/081284 A2 | 8/2006 |
| WO | WO 2006/108473 A1 | 10/2006 |
| WO | WO 2006/111512 A1 | 10/2006 |
| WO | WO 2006/128245 A1 | 12/2006 |
| WO | WO 2006/133022 A2 | 12/2006 |
| WO | WO 2006/137941 A2 | 12/2006 |
| WO | WO 2007/000668 A2 | 1/2007 |
| WO | WO 2007/016548 A2 | 2/2007 |
| WO | WO 2007/033023 A2 | 3/2007 |
| WO | WO 2007/042899 A2 | 4/2007 |
| WO | WO 2007/067695 A2 | 6/2007 |
| WO | WO 2007/070483 A2 | 6/2007 |
| WO | WO 2007/081680 A2 | 7/2007 |
| WO | WO 2007/081720 A2 | 7/2007 |
| WO | WO 2007/081740 A2 | 7/2007 |
| WO | WO 2007/109236 A2 | 9/2007 |
| WO | WO 2007/112754 A2 | 10/2007 |
| WO | WO 2008/016924 A2 | 2/2008 |
| WO | WO 2008/043521 A2 | 4/2008 |
| WO | WO 2008/061537 A2 | 5/2008 |
| WO | WO 2008/116267 A1 | 10/2008 |
| WO | WO 2008/147839 A1 | 12/2008 |
| WO | WO 2009/012263 A2 | 1/2009 |
| WO | WO 2009/026576 A1 | 2/2009 |
| WO | WO 2009/043353 A2 | 4/2009 |
| WO | WO 2009/058818 A2 | 5/2009 |
| WO | WO 2009/062169 A2 | 5/2009 |
| WO | WO 2009/111375 A2 | 9/2009 |
| WO | WO 2009/114681 A2 | 9/2009 |
| WO | WO 2009/121031 A1 | 10/2009 |
| WO | WO 2009/149182 A1 | 12/2009 |
| WO | WO 2010/036939 A2 | 4/2010 |
| WO | WO 2010/048585 A2 | 4/2010 |

OTHER PUBLICATIONS

Kim, "International Search Report," 4 pages, from International Patent Appl. No. PCT/US2008/071839, Korean Intellectual Property Office, Daejon, Republic of Korea (mailed Jan. 6, 2009).

Rooij et al., "A signature pattern of stress-responsive microRNAs that can evoke cardiac hypertrophy and heart failure," Proc. Natl. Acad. Sci. USA 103(48):18255-18260 (2006).

Tatsuguchi et al., "Expression of MicroRNAs is Dynamically Regulated During Cardiomyocyte Hypertrophy," J. Mol. Cell. Cardiol. 42(6):1137-1141 (2007).

Lagos-Quintana et al., "New microRNAs from mouse and human," RNA, vol. 9:175-179, 2003.

Lagos-Quintana et al., "Identification of tissue-specific microRNAs from mouse," Current Biology, vol. 12:735-739, 2002.

Sempere et al., "Expression profiling of mammalian microRNAs uncovers a subset of brain-expressed microRNAs with possible roles in murine and human neuronal differentiation," Genome Biology, vol. 5:R13, 2004.

Mott et al., "miR-29 regulates Mcl-1 protein expression and apoptosis," Oncogene, vol. 26: 6133-6140, 2007.

He et al., "Overexpression of Micro Ribonucleic Acid 29, Highly Up-Regulated in Diabetic Rats, Leads to Insulin Resistance in 3T3-L1 Adipocytes," Molecular Endocrinology, vol. 21: 2785-2794, 2007.

Zhao et al., "Dysregulation of Cardiogenesis, Cardiac Conduction, and Cell Cycle in Mice Lacking miRNA-1-2," Cell, vol. 129: 303-317, 2007.

Van Rooij et al., "Dysregulation of microRNAs after myocardial infarction reveals a role of miR-29 in cardiac fibrosis," Proc. Natl. Acad. Sci, USA, vol. 105: 13027-13032, 2008.

Spindler, Supplementary European Search Report for European Application No. 08797006.7, 10 pages, European Patent Office, The Hague, mailed Aug. 17, 2011.

Pekarsky Y. et al., "Tcl1 expression in chronic lymphocytic leukemia is regulated by miR-29 and miR-181," Cancer Research, vol. 66:11590-11593, 2006.

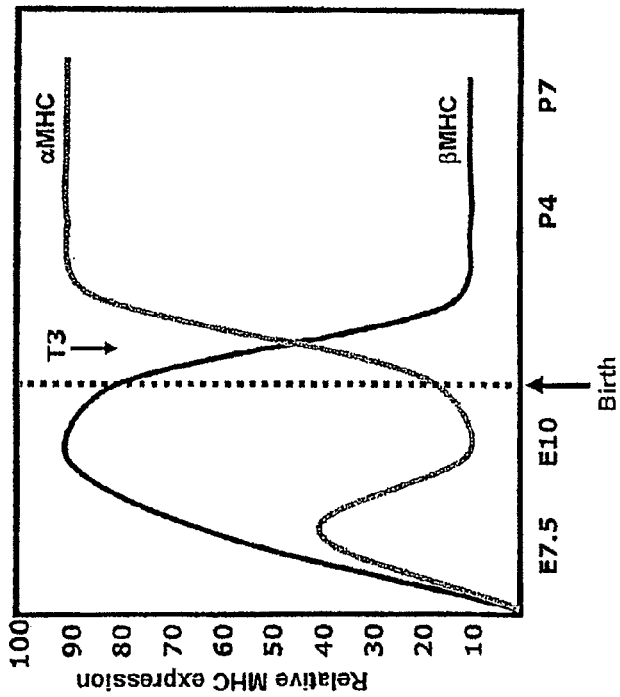
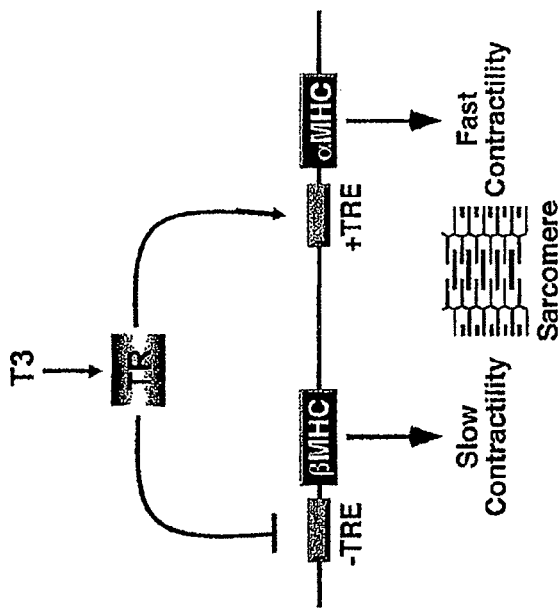
FIG. 2A

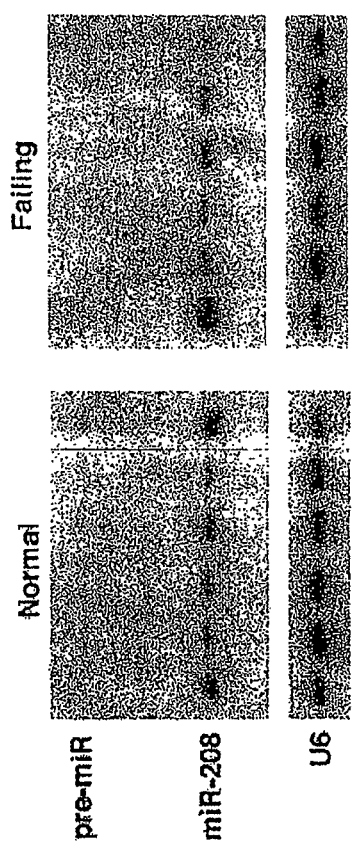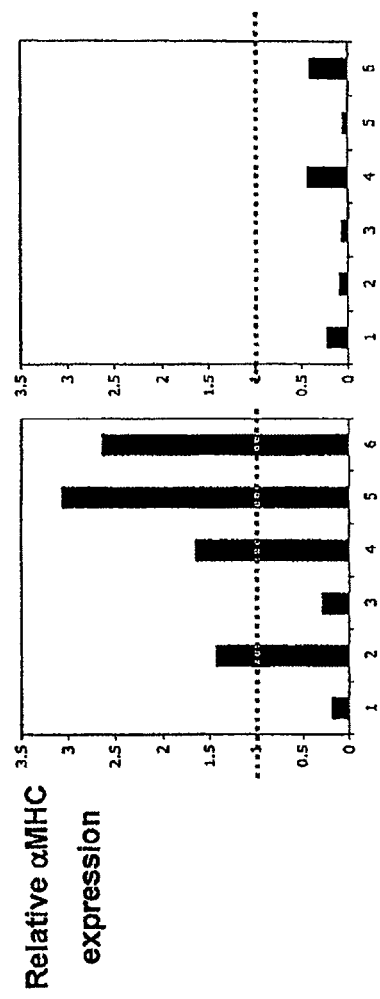
FIG. 3

FIG. 4A-B

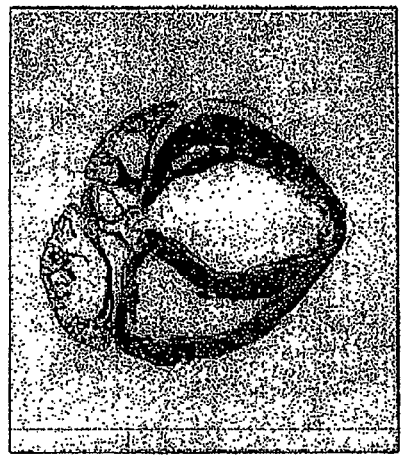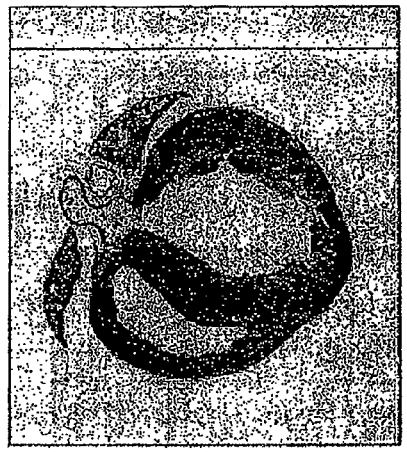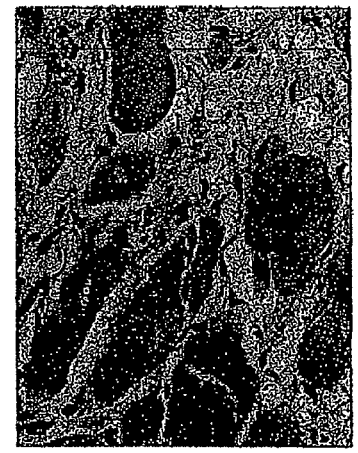
FIG. 7

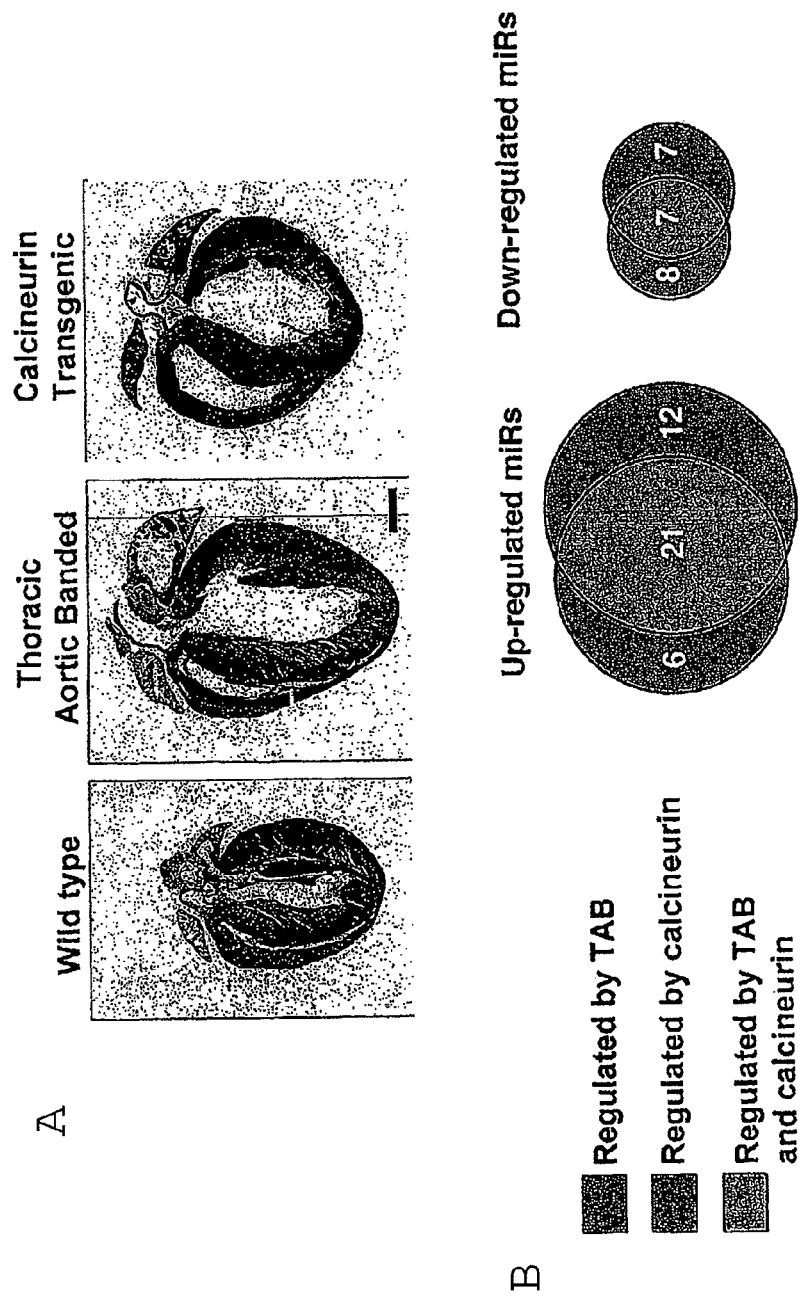
FIG. 14A-B

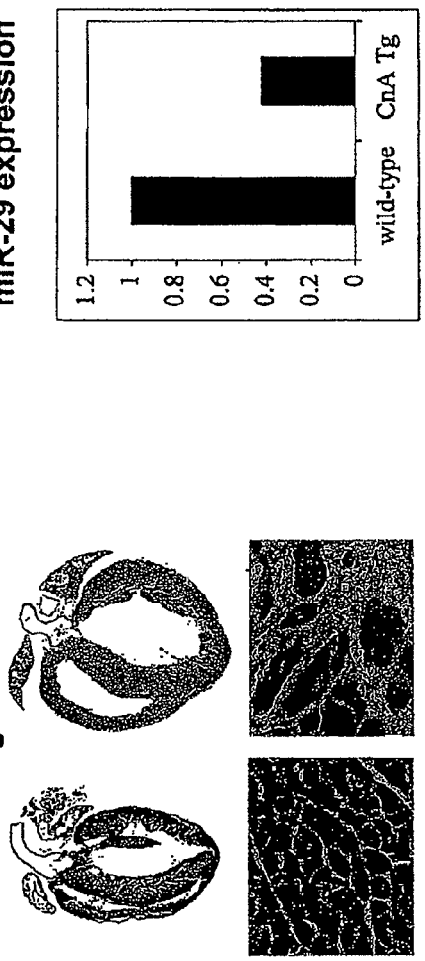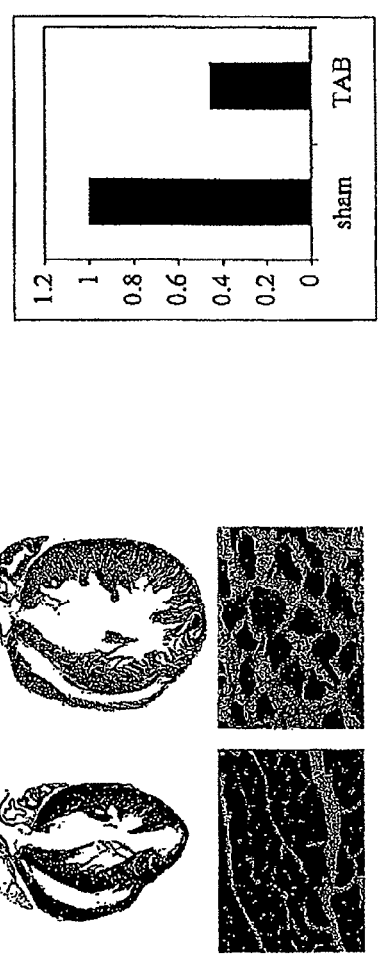
FIG. 15

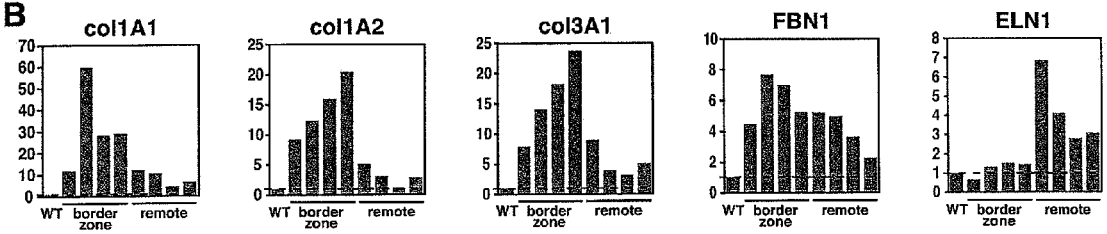
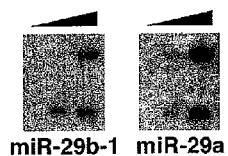
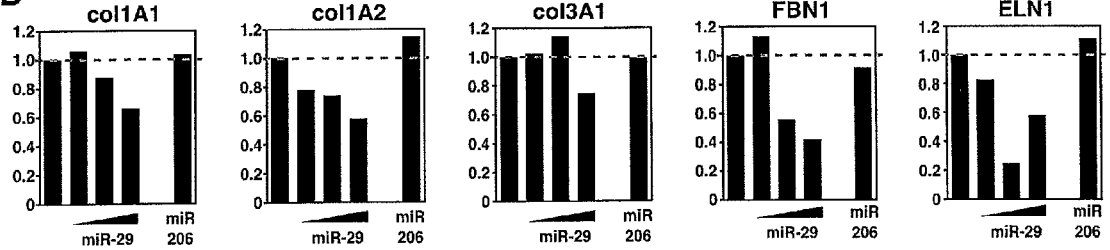
FIG. 20A-D

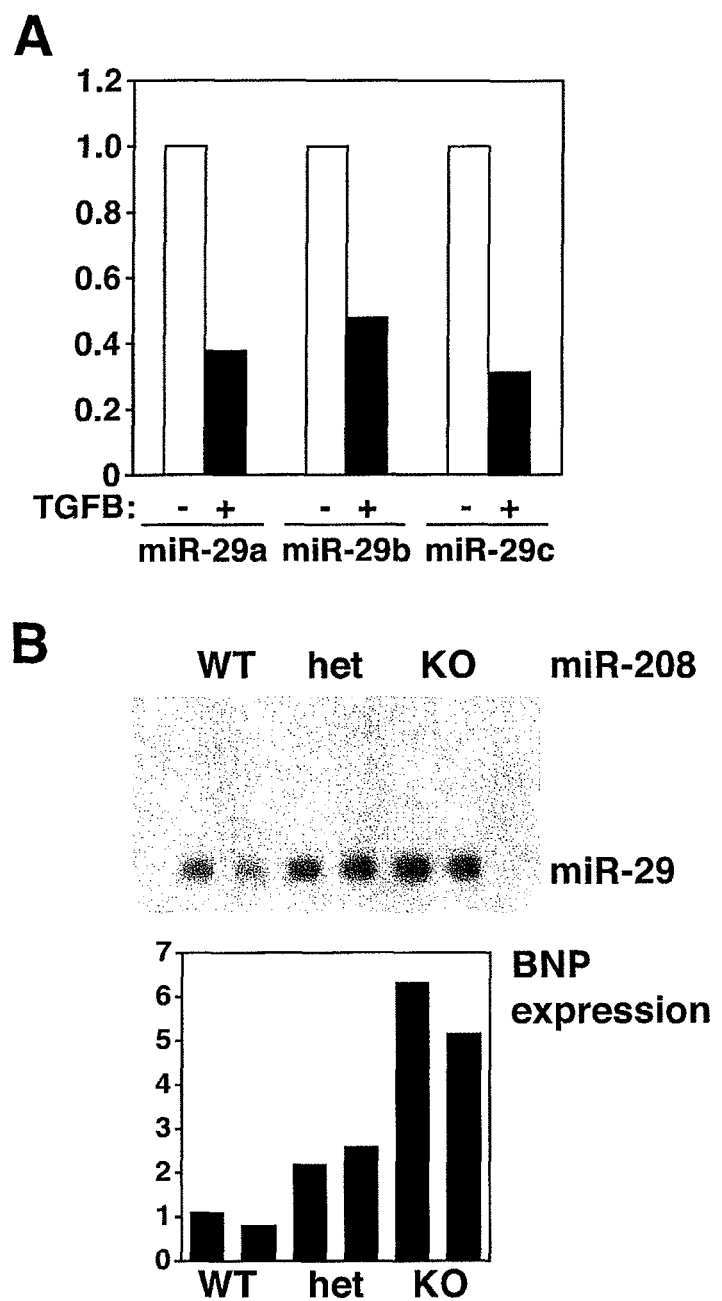
FIG. 21A-B

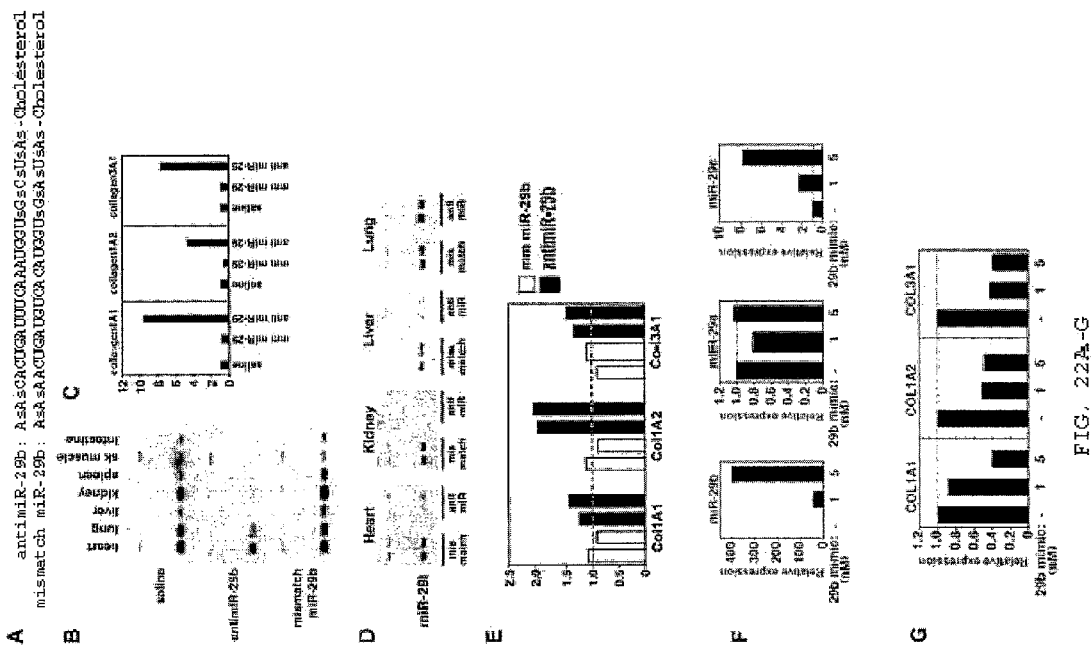
FIG. 22A-G

SEQUENCE LISTING

<160> NUMBER OF SEQ ID NOS: 22

<210> SEQ ID NO 1
<211> LENGTH: 71
<212> TYPE: DNA
<213> ORGANISM: Homo sapiens

<400> SEQUENCE: 1
tgacgggcga gcttttggcc cgggttatac ctgatgctca cgtataagac gagcaaaaag      60
cttgttggtc a      71

<210> SEQ ID NO 2
<211> LENGTH: 71

```
<212> TYPE: DNA
<213> ORGANISM: Mus sp.

<400> SEQUENCE: 2
tgacgggtga gcttttggcc cgggttatac ctgactctca cgtataagac gagcaaaaag      60
cttgttggtc a                                                           71

<210> SEQ ID NO 3
<211> LENGTH: 71
<212> TYPE: DNA
<213> ORGANISM: Rattus sp.

<400> SEQUENCE: 3
tgacgggtga gcttttggcc cgggttatac ctgactctca cgtataagac gagcaaaaag      60
cttgttggtc a                                                           71

<210> SEQ ID NO 4
<211> LENGTH: 71
<212> TYPE: DNA
<213> ORGANISM: Canis sp.

<400> SEQUENCE: 4
tgacgcatga gcttttggct cgggttatac ctgatgctca cgtataagac gagcaaaaag      60
cttgttggtc a                                                           71

<210> SEQ ID NO 5
<211> LENGTH: 22
<212> TYPE: RNA
<213> ORGANISM: Unknown
<220> FEATURE:
<223> OTHER INFORMATION: miR-208 sequence

<400> SEQUENCE: 5
auaagacgag caaaaagcuu gu                                               22

<210> SEQ ID NO 6
<211> LENGTH: 69
<212> TYPE: RNA
<213> ORGANISM: Homo sapiens

<400> SEQUENCE: 6
uucuugcuuu aaagcaauug gucuaaaaua uauguaaucg ucuuaauuaa aaaguugcag      60
uagguuugc                                                              69

<210> SEQ ID NO 7
<211> LENGTH: 69
<212> TYPE: RNA
<213> ORGANISM: Pan sp.

<400> SEQUENCE: 7
uucuugcuuu aaagcaauug gucuaaaaua uauguaaucg ucuuaauuaa aacguugcag      60
uagguuugc                                                              69

<210> SEQ ID NO 8
<211> LENGTH: 69
<212> TYPE: RNA
<213> ORGANISM: Mus sp.

<400> SEQUENCE: 8
uucuugcuuu aaagcaauug gucuaaaaua uauguaaucg ucuuaauuaa aacguugcag      60
``` uaggguugc 69

<210> SEQ ID NO 9
<211> LENGTH: 69
<212> TYPE: RNA
<213> ORGANISM: Rattus sp.

<400> SEQUENCE: 9
uucuugcuuu aaagcaauug gucuaaaaua uauguaaucg ucuuaauuaa aacguugcag    60
uaggguugc                                                           69

<210> SEQ ID NO 10
<211> LENGTH: 69
<212> TYPE: RNA
<213> ORGANISM: Canis sp.

<400> SEQUENCE: 10
uucuugcuuu aaagcaauug gucuaaaaua uauguaaucg ucuuaauuaa aacguugcag    60
uaggguugc                                                           69

<210> SEQ ID NO 11
<211> LENGTH: 69
<212> TYPE: RNA
<213> ORGANISM: Gallus sp.

<400> SEQUENCE: 11
uucuugcuuu aaagcaauug gucuaaaaua uauguaaucg ucuuaauuaa aacguugcag    60
uaggguugc                                                           69

<210> SEQ ID NO 12
<211> LENGTH: 72
<212> TYPE: RNA
<213> ORGANISM: Takifugu

<400> SEQUENCE: 12
uuccugcuuu aagcaauugg uugaaaauau auguauguaa uggucuuaau uaaaaaaaca    60
aacuaagaca aa                                                       72

<210> SEQ ID NO 13
<211> LENGTH: 69
<212> TYPE: RNA
<213> ORGANISM: Danio sp.

<400> SEQUENCE: 13
uuccugcuuu aaagcaauug gucuaaaaua uauguaaucg ucuucauuac aaaaacgaac    60
caucaaacg                                                           69

<210> SEQ ID NO 14
<211> LENGTH: 71
<212> TYPE: DNA
<213> ORGANISM: Homo sapiens

<400> SEQUENCE: 14
acgggcgagc ttttggcccg ggttatacct gatgctcacg tataagacga gcaaaaagct    60
tgttggtcag a                                                        71

<210> SEQ ID NO 15
<211> LENGTH: 71
<212> TYPE: DNA
<213> ORGANISM: Mus sp.

```
<400> SEQUENCE: 15
acgggtgagc ttttggcccg ggttatacct gactctcacg tataagacga gcaaaaagct    60
tgttggtcag a                                                          71

<210> SEQ ID NO 16
<211> LENGTH: 71
<212> TYPE: DNA
<213> ORGANISM: Rattus sp.

<400> SEQUENCE: 16
acgggtgagc ttttggcccg ggttatacct gactctcacg tataagacga gcaaaaagct    60
tgttggtcag a                                                          71

<210> SEQ ID NO 17
<211> LENGTH: 71
<212> TYPE: DNA
<213> ORGANISM: Canis sp.

<400> SEQUENCE: 17
acgcatgagc ttttggctcg ggttatacct gatgctcacg tataagacga gcaaaaagct    60
tgttggtcag a                                                          71

<210> SEQ ID NO 18
<211> LENGTH: 22
<212> TYPE: RNA
<213> ORGANISM: Homo sapiens

<400> SEQUENCE: 18
uagcaccauc ugaaaucggu ua                                              22

<210> SEQ ID NO 19
<211> LENGTH: 23
<212> TYPE: RNA
<213> ORGANISM: Homo sapiens

<400> SEQUENCE: 19
uagcaccauu ugaaaucagu guu                                             23

<210> SEQ ID NO 20
<211> LENGTH: 22
<212> TYPE: RNA
<213> ORGANISM: Homo sapiens

<400> SEQUENCE: 20
uagcaccauu ugaaaucggu ua                                              22

<210> SEQ ID NO 21
<211> LENGTH: 71
<212> TYPE: RNA
<213> ORGANISM: Unknown
<220> FEATURE:
<223> OTHER INFORMATION: Pre miR-208 sequence

<400> SEQUENCE: 21
ugacgggcga gcuuuuggcc cggguuauac cugaugcuca cguauaagac gagcaaaaag    60
cuuguugguc a                                                          71

<210> SEQ ID NO 22
<211> LENGTH: 27
<212> TYPE: RNA
```

```
<213> ORGANISM: Homo sapiens

<400> SEQUENCE: 22
uagcaccauu ugaaagaaau caguguu                                             27
```

US 8,940,712 B2

MICRO-RNA FAMILY THAT MODULATES FIBROSIS AND USES THEREOF

CROSS-REFERENCE TO RELATED APPLICATIONS

This application is a continuation of U.S. application Ser. No. 12/671,445, filed Jan. 29, 2010, which is a national stage application of International Application No. PCT/US2008/071839, filed Jul. 31, 2008, which claims the benefit of U.S. Provisional Application No. 60/952,917, filed Jul. 31, 2007; U.S. Provisional Application No. 60/980,303, filed Oct. 16, 2007, and U.S. Provisional Application No. 61/047,014, filed Apr. 22, 2008, all of which are herein incorporated by reference in their entireties.

STATEMENT OF GOVERNMENT SUPPORT

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (file-name: MIRG_005_05US_SeqList_ST25.txt, date recorded: Mar. 15, 2013, file size 5 kilobytes).

FIELD OF THE INVENTION

The present invention relates generally to the fields of developmental biology and molecular biology. More particularly, it concerns gene regulation and cellular physiology in fibroblasts by the miR-29 family. This miRNA family plays an important role in collagen deposition, particularly collagen deposition mediated by fibroblasts.

BACKGROUND OF THE INVENTION

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. Although initial collagen deposition is required for infarct healing and to prevent cardiac rupture, the continuous production of collagen by fibroblasts induces interstitial fibrosis surrounding the myocytes in the infarct borderzone and remote myocardium of the infracted heart. This fibrosis induces stiffness, diastolic dysfunction, and cardiomyocyte hypertrophy due to the increase in stress and can also lead to arrythmias.

Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%. The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and cardiac heart failure.

Treatment with pharmacological agents represents the primary mechanism for reducing or eliminating the manifestations of heart failure. Diuretics constitute the first line of treatment for mild-to-moderate heart failure. If diuretics are ineffective, vasodilatory agents, such as angiotensin converting enzyme (ACE) inhibitors (e.g., enalopril and lisinopril) or inotropic agent therapy (i.e., a drug that improves cardiac output by increasing the force of myocardial muscle contraction) may be used. Unfortunately, many of these standard therapies have numerous adverse effects and are contraindicated in some patients. Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities.

Cardiac myocytes are normally surrounded by a fine network of collagen fibers. In response to pathological stress, cardiac fibroblasts and extracellular matrix proteins accumulate disproportionately and excessively. Myocardial fibrosis, a characteristic of all forms of pathological hypertrophy, leads to mechanical stiffness, which contributes to contractile dysfunction (Abraham et al., 2002). Another hallmark of pathological hypertrophy and heart failure is the re-activation of a set of fetal cardiac genes, including those encoding atrial natriuretic peptide (ANP), B-type natriuretic peptide (BNP) and fetal isoforms of contractile proteins, such as skeletal α-actin and β-myosin heavy chain (MHC). These genes are typically repressed post-natally and replaced by the expression of a set of adult cardiac genes (McKinsey and Olson, 2005). The consequences of fetal gene expression on cardiac function and remodeling (e.g., fibrosis) are not completely understood. However, the up-regulation of β-MHC, a slow ATPase, and down-regulation of α-MHC, a fast contracting ATPase, in response to stress has been implicated in the diminution of cardiac function (Bartel, 2004) and BNP is known to play a dominant role in cardiac fibrosis.

In addition to cardiac fibrosis, there are a number of disorders or conditions that are associated with fibrosis of various tissues. Congenital hepatic fibrosis, an autosomal recessive disease, is a rare genetic disease that affects both the liver and kidneys. The disease is characterized by liver abnormalities, such as hepatomegaly, portal hypertension, and fiber-like connective tissue that spreads over and through the liver (hepatic fibrosis). Pulmonary fibrosis, or scarring of the lung, results from the gradual replacement of normal lung air sacs with fibrotic tissue. When the scar forms, the tissue becomes thicker, causing an irreversible loss of the tissue's ability to transfer oxygen into the bloodstream. The most current thinking is that the fibrotic process in pulmonary tissue is a reaction (predisposed by genetics) to microscopic injury to the lung. While the exact cause remains unknown, associations have been made with inhaled environmental and occupational pollutants, cigarette smoking, diseases such as scleroderma, rheumatoid arthritis, lupus and sarcoidosis, certain medications and therapeutic radiation.

Scleroderma is a chronic disease characterized by excessive deposits of collagen in the skin or other organs. The localized type of the disease, while disabling, tends not to be fatal. The systemic type or systemic sclerosis, which is the generalized type of the disease, can be fatal as a result of heart, kidney, lung or intestinal damage. Scleroderma affects the skin, and in more serious cases it can affect the blood vessels and internal organs.

Skeletal muscle fibrosis is a phenomenon which frequently occurs in diseased or damaged muscle. It is characterized by the excessive growth of fibrous tissue which usually results from the body's attempt to recover from injury. Fibrosis impairs muscle function and causes weakness. The extent of loss of muscle function generally increases with the extent of fibrosis. Victims of muscular dystrophies, particularly Becker muscular dystrophy (BMD) and the more severely penetrating allelic manifestation, Duchenne muscular dystrophy (DMD), frequently suffer from increasing skeletal muscle fibrosis as the disease progresses. Other afflictions such as denervation atrophy are known to produce skeletal muscle fibrosis, as well as neuromuscular diseases, such as acute polyneuritis, poliomyelitis, Werdig/Hoffman disease, amyotrophic lateral sclerosis (Lou Gehrig's Disease), and progressive bulbar atrophy disease.

MicroRNAs have recently been implicated in a number of biological processes including regulation of developmental timing, apoptosis, fat metabolism, and hematopoietic cell differentiation among others. MicroRNAs (miRs) are small, non-protein coding RNAs of about 18 to about 25 nucleotides in length that are derived from individual miRNA genes, from introns of protein coding genes, or from poly-cistronic transcripts that often encode multiple, closely related miRNAs. See review of Carrington et al. (2003). MiRs act as repressors of target mRNAs by promoting their degradation, when their sequences are perfectly complementary, or by inhibiting translation, when their sequences contain mismatches.

miRNAs are transcribed by RNA polymerase II (pol II) or RNA polymerase III (pol III; see Qi et al. (2006) Cellular & Molecular Immunology Vol. 3:411-419) and arise from initial transcripts, termed primary miRNA transcripts (pri-miRNAs), that are generally several thousand bases long. PrimiRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Krania, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs. Enhanced understanding of the functions of miRNAs will undoubtedly reveal regulatory networks that contribute to normal development, differentiation, inter- and intra-cellular communication, cell cycle, angiogenesis, apoptosis, and many other cellular processes. Recently, the inventors reported a cardiac-specific microRNA, miR-208, which is encoded by an intron of the α-myosin heavy chain (MHC) gene, and is required for up-regulation of β-MHC expression in response to cardiac stress and for repression of fast skeletal muscle genes in the heart (see co-pending application WO2008/016924, which is herein incorporated by reference in its entirety). The present invention expands on the involvement of microRNAs in the heart as well as other tissues.

SUMMARY OF THE INVENTION

The present invention is based on the discovery that the miR-29 family, which is down-regulated in the heart in response to stress, regulates collagen deposition and the development of fibroses, including cardiac fibrosis. Up-regulation of miR-29a-c expression or function results in the decrease of expression of collagen and fibrin genes leading to reduced cardiac fibrosis. Accordingly, the present invention provides a method of treating cardiac fibrosis, cardiac hypertrophy, or heart failure in a subject in need thereof comprising identifying a subject having cardiac fibrosis, cardiac hypertrophy or heart failure; and administering to said subject an agonist of miR-29a-c expression or function. In one embodiment, the agonist of miR-29a-c is a polynucleotide comprising the mature sequence of miR-29a, miR-29b, miR-29c, or combinations thereof. The agonist of miR-29a-c may be administered by parenteral administration (e.g. intravenous or subcutaneous), oral, transdermal, sustained release, controlled release, delayed release, suppository, catheter or sub-lingual administration. In another embodiment, the method further comprises administering to the subject a second therapy. The second therapy is selected from the group consisting of a beta blocker, an ionotrope, a diuretic, ACE-I, AII antagonist, BNP, a $Ca^{++}$-blocker, an endothelin receptor antagonist, and an HDAC inhibitor.

The present invention also provides a method of preventing pathologic hypertrophy or heart failure in a subject in need thereof comprising identifying a subject at risk of developing pathologic cardiac hypertrophy or heart failure; and promoting the expression or activity of miR-29a-c in cardiac cells of said subject. In one embodiment, the promoting expression or activity of miR-29a-c comprises delivering to the cardiac cells an agonist of miR-29a-c or an expression vector encoding miR-29a-c. In another embodiment, the subject at risk exhibits one or more risk factors selected from the group consisting of long standing uncontrolled hypertension, uncorrected valvular disease, chronic angina, recent myocardial infarction, congenital predisposition to heart disease, and pathological hypertrophy. In another embodiment, the subject at risk has been diagnosed as having a genetic predisposition to cardiac hypertrophy. In still another embodiment, the subject at risk has a familial history of cardiac hypertrophy.

The present invention also encompasses a transgenic, non-human mammal, the cells of which fail to express a functional miR-29a, miR29b, and/or miR29c. In another embodiment, the invention provides a transgenic, non-human mammal, the cells of which comprise a miR-29a-c coding region under the control of a heterologous promoter active in the cells of said non-human mammal. The transgenic mammal may be a mouse.

In one embodiment, the present invention provides a method of treating myocardial infarction in a subject in need thereof comprising promoting expression or activity of miR-29a-c in cardiac cells of said subject. In another embodiment, the present invention provides a method of preventing cardiac hypertrophy and dilated cardiomyopathy in a subject in need thereof comprising promoting expression or activity of miR-29a-c in cardiac cells of said subject. In another embodiment, the present invention provides a method of inhibiting progression of cardiac hypertrophy in a subject in need thereof comprising promoting expression or activity of miR-29a-c in cardiac cells of said subject.

The present invention also contemplates a method of treating or preventing a tissue fibrosis in a subject comprising identifying a subject having or at risk of tissue fibrosis; and increasing the expression and/or activity of miR-29a-c in skeletal muscle or fibroblast cells of the subject. The tissue fibrosis may be cardiac fibrosis, scleroderma, skeletal muscle fibrosis, hepatic fibrosis, kidney fibrosis, pulmonary fibrosis, or diabetic fibrosis. In some embodiments, increasing the expression and/or activity of miR-29a-c comprises administering an agonist of miR-29a-c to the subject. An agonist of miR-29a-c may be a polynucleotide comprising the sequence of a mature miR-29a, miR-29b, and/or miR-29c sequence. The agonist of miR-29a-c may also be an expression vector encoding miR-29a, miR-29b, and/or miR-29c. In one embodiment, the method further comprises administering a non-miR-29a-c anti-fibrotic therapy to the subject.

The present invention also provides a method for identifying a modulator of miR-29a-c comprising contacting a cell with a candidate compound; assessing miR-29a-c activity or expression; and comparing the activity or expression in step (b) with the activity or expression of miR-29a-c in the absence of the candidate compound, wherein a difference between the measured activities or expression of miR-29a-c indicates that the candidate compound is a modulator of miR-29. The cell may be contacted with the candidate compound in vitro or in vivo. Suitable candidate compounds include proteins, peptides, polypeptides, polynucleotides, oligonucleotides or small molecules.

The present invention also encompasses a pharmaceutical composition comprising an agonist or antagonist of miR-29a-c. In some embodiments, the pharmaceutical composition may be formulated for injection or topical administration. The formulation for topical administration may be a gel, cream, lotion, or ointment.

The present invention provides a method of inducing collagen deposition in a tissue comprising contacting said tissue with an antagonist of miR-29a-c. The antagonist may be an antagonist of miR-29a, miR-29b, or miR-29c. The antagonist may be an antagomir of miR-29a-c, an antisense oligonucleotide that targets a mature miR-29a-c sequence, or an inhibitory RNA molecule, such as a siRNA or shRNA, that comprises a sequence identical to a mature miR-29a-c sequence, or a ribozyme or another inhibitory nucleic acid. In one embodiment, the method further comprises contacting said tissue with a second agent. The second agent may be topical vitamin A, topical vitamin C, or vitamin E. In another embodiment, the method further comprises subjecting said tissue to a second treatment, such as a chemical peel, laser treatment, dermaplaning, or dermabrasion. In another embodiment, the tissue is in a subject that suffers from Ehler's-Danlos syndrome or Vitamin C deficiency.

BRIEF DESCRIPTION OF THE DRAWINGS

The invention may be better understood by reference to one or more of these drawings in combination with the detailed description of specific embodiments presented herein.

(FIG. 1A) miR-208 is encoded within an intron of the α-MHC gene. Asterisks indicate sequence conservation (SEQ ID NOS:1-5). (FIG. 1B) Detection of miR-208 transcripts by Northern analysis of adult mouse tissues. U6 mRNA serves as a loading control.

FIGS. 2A-B. Regulation of α- and β-MHC. (FIG. 2A) Regulation of class switch by thyroid hormone and TRE. (FIG. 2B) Model for stress/hypothyroidism in fast-to-slow muscle fiber contactility switch.

FIG. 3. Detection of miR-208 in human heart. Transcripts for α-MHC and miR-208 were detected by Northern blot of cardiac tissue from six normal individuals and six individuals with idiopathic cardiomyopathy. A close correlation exists between the level of expression of α-MHC and pre-miR-208, whereas mature miR-208 expression is maintained after the latter has been down-regulated.

(FIG. 4A) Strategy to generate miR-208 mutant mice by homologous recombination. The pre-miRNA sequence (located within intron 29 of the mouse α-MHC gene in most transcripts) was replaced with a neomycin resistance cassette flanked by loxP sites. The neomycin cassette was removed in the mouse germline by breeding heterozygous mice to transgenic mice harboring the CAG-Cre transgene. (FIG. 4B) Detection of miR-208 transcripts by Northern analysis of hearts from wild-type and miR-208 mutant mice.

FIG. 7. MiR-208$^{-/-}$ mice show reduced cardiac hypertrophy in response to calcineurin activation. Histological sections of hearts of 6 week-old mice expressing a calcineurin transgene (CnA-Tg) and hearts of miR-208$^{-/-}$; CnA-Tg stained for Masson trichrome. Absence of miR-208 diminishes hypertrophy and fibrosis seen in CnA-Tg mice. Scale bar=2 mm for top panel, 20 μm for bottom panel.

FIGS. 14A-C. mRNA expression during cardiac hypertrophy and remodeling. (FIG. 14A) H&E stained sections of representative hearts from mice following sham and TAB for 21 days and from CnA Tg mice. Scale bar equals 2 mm. (FIG. 14B) Venn diagrams showing numbers of microRNAs that changed in expression in each type of heart are shown below. (FIG. 14C) Northern blots of microRNAs that change in expression during hypertrophy. U6 RNA was detected as a loading control.

FIG. 15. miR-29a-c expression is down-regulated in response to cardiac stress. Hearts from wild-type mice (WT) and mice with hypertrophy and fibrosis induced by a calcineurin transgene (CnA) or TAB are shown on the left. The relative level of expression of miR-29a-c in each type of heart is shown on the right.

FIGS. 20A-D. miR-29a-c regulates the expression of extracellular matrix proteins. (FIG. 20A) Potential binding sites for miR-29a-c in 3' UTR regions of key fibrotic genes. (FIG. 20B) Real-time PCR analysis of predicted target genes in both the borderzone and remote myocardium 3 days after MI, shows a decrease in miR-29a-c to correlate to an increase in collagens (COL1A1, COL1A2 and COL3A1) and fibrillin (FBN1), while there was no significant change in elastin (ELN1). (FIG. 20C) Northern blot analysis on COS cells transfected with increasing amounts of the CMV expression plasmid encoding the miR-29b-1/miR-29a cluster, shows efficient overexpression of miR-29a-b. The top band corresponds to the pre-miRNA, while the lower band corresponds to the mature miRNA. (FIG. 20D) Luciferase experiments using the endogenous UTR sequences of the predicted target genes, showing miR-29a-c to repress expression of luciferase in response to increasing amounts of miR-29a-c while this decrease was absent when using an unrelated miR, miR-206.

FIGS. 21A-B. miR-29a-c expression responsive to TGFβ. (FIG. 21A) Real-time PCR analysis indicates that all three miR-29 family members are downregulated in fibroblasts in response to TGFβ. (FIG. 21B) Northern analysis showing miR-29a-c expression is upregulated in miR-208 mutant animals which coincides with an increase in BNP expression as determined by real-time PCR.

FIGS. 22A-G. miR-29a-c inhibition induces fibrosis in vivo. (FIG. 22A) Chemical structure of anti-miR-29a-c and mismatch (mm) miR-29a-c. (FIG. 22B) Northern blot analysis showing tissue specific knockdown after 3 days in response to intravenous injection of 80 mg/kg of either anti-miR-29a-c or mm miR-29a-c or a comparable volume of saline. (FIG. 22C) Real-time PCR analysis of liver extracts indicate a pronounced increase in collagen expression in response to miR-29a-c knockdown, while this effect was absent after saline or mm injection. (FIG. 22D) Tissue collection, three weeks after intravenous injection with 80 mg/kg on two consecutive days of either anti-miR-29a-c or mm miR-29a-c oligonucleotide or a comparable volume of saline, indicates a severe knockdown of miR-29a-c in heart, liver and kidney, while miR-29a-c levels in lungs appear unaffected. (FIG. 22E) Real-time PCR analysis of heart extracts indicate a increase in cardiac collagen expression in response to miR-29a-c knockdown. (FIG. 22F) Real-time PCR analysis indicating an increase in miR-29b expression in fibroblasts two days after miR-29b mimic treatment, while miR-29a levels were unchanged and miR-29c levels only slightly increased. (FIG. 22G) miR-29b overexpression in fibroblasts represses the expression of collagen genes as determined by real-time PCR analysis.

DETAILED DESCRIPTION OF ILLUSTRATIVE EMBODIMENTS

Figure 1:
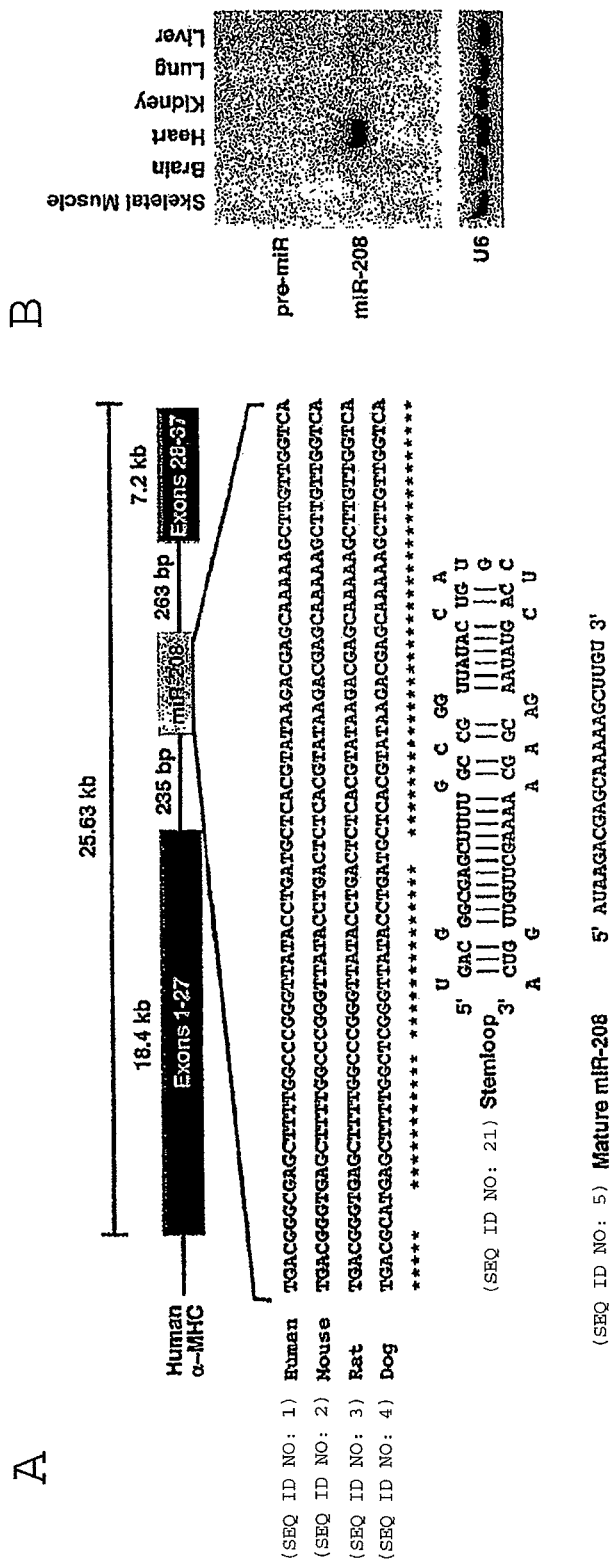
FIGS. 1A-B. miR-208 is encoded by the α-MHC gene and is expressed specifically in the heart.
Figure 2B:
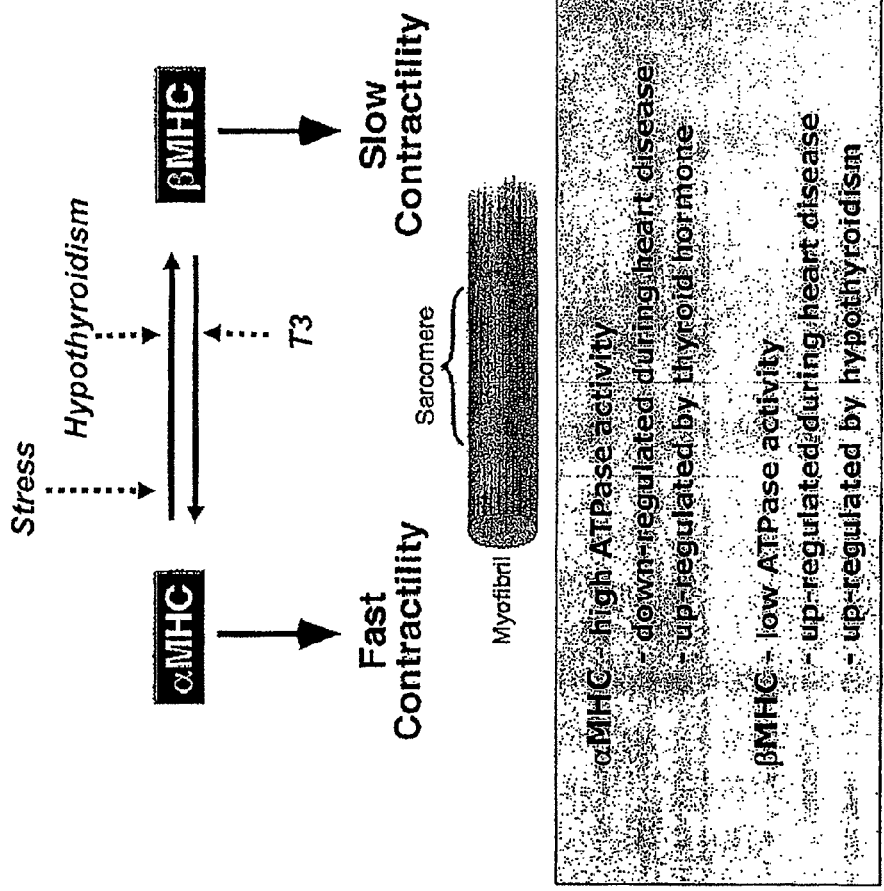
Figure 4:
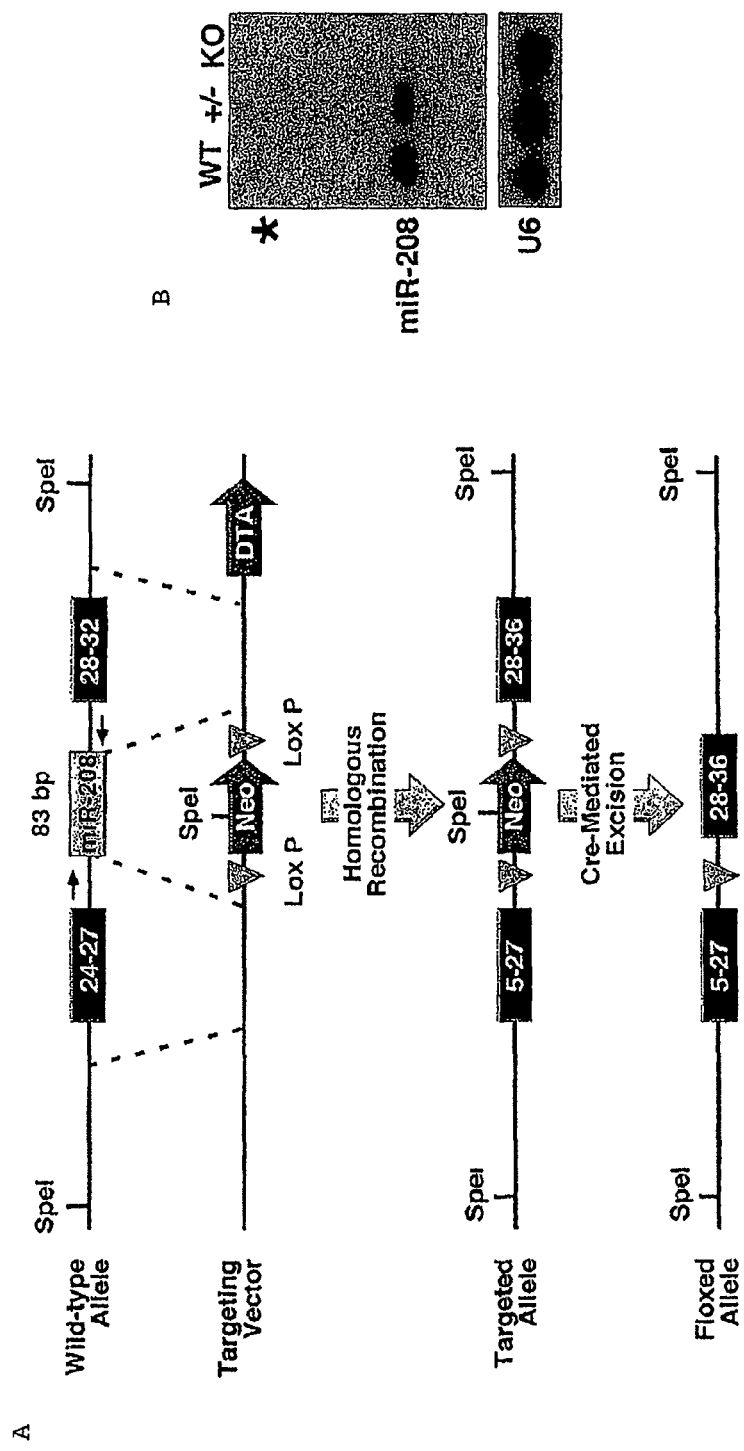
FIGS. 4A-B. Generation of miR-208 mutant mice.

Cardiac and skeletal muscles respond to a variety of pathophysiological stimuli such as workload, thyroid hormone signaling and injury by modulating the expression of myosin isoforms, which regulate the efficiency of contraction. Recently, the inventors reported a cardiac-specific microRNA, miR-208, which is encoded by an intron of the α-myosin heavy chain (MHC) gene, and is required for upregulation of β-MHC expression in response to cardiac stress and for repression of fast skeletal muscle genes in the heart (see co-pending application WO2008/016924, which is herein incorporated by reference in its entirety).

Here, the inventors extend their earlier work and show that miR-208 also down-regulates a family of related miRNAs, miR-29a-c. Because miR-29a-c are expressed ubiquitously, and are involved in regulation of collagen deposition, strategies to upregulate miR-29a-c expression have applications in the prevention of a variety of tissue fibroses including cardiac fibrosis, as well as skeletal muscle, liver, pulmonary, diabetic and kidney fibrosis. Regulation of miR-29a-c in cardiac cells, such as cardiac fibroblasts, can be used to treat or prevent cardiac hypertrophy or heart failure in a subject. Thus, one aspect of the invention is agonism of miR-29a-c expression or activity, optionally in conjunction with inhibiting miR-208. Agonism may involve introducing exogenous miR-29a-c into the heart or other tissues of interest, either directly using naked nucleic acid or a delivery vehicle such as a lipid/liposome/nanoparticle, or through gene expression, for example by using adenoviral vectors or other means of ectopic expression to reduce fibrosis. Activation of the anti-fibrotic function of miR-29a-c through pharmaceutical "small molecules" also is contemplated, as are screens to identify such compounds.

The increase in collagen that ensues following repression of miR-29a-c expression, for example, following myocardial infarction (MI) and other forms of stress, may indicate another role for miR-29a-c. One focus of the inventors' work is cardiac fibrosis, and an examination of a subset of key regulatory genes, namely collagen I, III, elastin and fibrillin, showed a striking increase in both collagens and fibrillin in response to miR-29a-c downregulation, while there was no increase in elastin. As such, therapeutically repressing miR-29a-c to increase collagen deposition presents a unique option for addressing conditions characterized by loss of collagen, such as in cosmetic applications and scarring.

MicroRNA 29 (miR-29) is a family of microRNAs that consists of 4 known members, miR-29a, b1 and 2 (identical) and c. While miR29b-1 and 29a stem from the same transcript originating from chromosome 7 in humans and chromosome 6 in mice, the miRNA cluster containing miR29b-2 and miR29c is transcribed from chromosome 1 in both species. The mature miRNA sequences for each of the human miR-29 family members is listed below:

```
hsa-miR-29a
                                        (SEQ ID NO: 18)
uagcaccaucugaaaucgguua hsa-miR-29b-1 and b-2
                                        (SEQ ID NO: 19)
uagcaccauuugaaaucaguguu hsa-miR-29c
                                        (SEQ ID NO: 20)
uagcaccauuugaaaucgguua
```

These microRNAs form a family based on their sequence homology (Yu et al; 2006). Since there are only minor differences between the family members, and the members have a 100% conserved seed region (which helps to define target determination), they are very likely to target the same mRNA targets (FIG. 18), and lower gene expression of these specific target genes. Target determination for the miR-29 family revealed that the miR-29 family shows a high preference for targeting genes involved in collagen formation as well as other extracellular matrix proteins, such as elastin (ELN), fibrillin 1 (FBN1), collagen type I, α1 and α2 (COL1A1, COL1A2) collagen type III, α1 (COL3A1), metallopeptidases, and integrins. In response to pathological stress, cardiac fibroblasts and extracellular matrix proteins accumulate disproportionately and excessively. Myocardial fibrosis, a characteristic of all forms of pathological hypertrophy, leads to mechanical stiffness, which contributes to contractile dysfunction (Berk et al., 2007). Since the miR-29 family is down-regulated during this remodeling process, this family is likely to play an active role in the modulation of collagen deposition, and thereby regulate cardiac fibrosis and cardiac contractility, which secondarily can induce hypertrophy and pathological remodeling.

As discussed previously, miR-208 appears to regulate miR-29 expression as miR-29 is significantly up-regulated in the hearts of mice lacking both copies of miR-208 (see Example 1). Thus, modulation of miR-208 can affect the expression of miR-29 as well as the expression of miR-29 target genes. MiR-208 is an intronic miRNA that is located within an intron of the α-MHC gene. The precise intron location is dependent on the particular species and specific transcript. For example, in humans, miR-208 is encoded within the 28$^{th}$ intron of the α-MHC gene, while in mice, it is encoded within the 29$^{th}$ intron. The pre-miRNA encoding sequences for miR-208 for human, mouse, rat, and canine are provided in SEQ ID NO:14, SEQ ID NO:15, SEQ ID NO:16, SEQ ID NO:17, respectively. The mature miR-208 sequence is provided in SEQ ID NO:5. Like α-MHC, miR-208 is expressed solely in the heart. (FIG. 1).

```
Human pre-miR-208
                                        (SEQ ID NO: 14)
acgggcgagc ttttgcccg ggttatacct gatgctcacg tataagacga gcaaaaagct tgttggtcag a Mouse pre-miR-208
                                        (SEQ ID NO: 15)
acgggtgagc ttttgcccg ggttatacct gactctcacg tataagacga gcaaaaagct tgttggtcag a Rat pre-miR-208
                                        (SEQ ID NO: 16)
acgggtgagc ttttgcccg ggttatacct gactctcacg tataagacga gcaaaaagct tgttggtcag a Canine pre-miR-208
                                        (SEQ ID NO: 17)
acgcatgagc ttttggctcg ggttatacct gatgctcacg tataagacga gcaaaaagct tgttggtcag a
```

Using the PicTar algorithm for the identification of miRNA targets (Krek et al., 2005), the inventors identified thyroid hormone receptor associated protein 1 (THRAP1) as a predicted target for miR-208. THRAP1 3' UTR sequences from human, chimp, mouse, rat, canine, chicken, fugu, and zebrafish are provided in SEQ ID NO:6, SEQ ID NO:7, SEQ ID NO:8, SEQ ID NO:9, SEQ ID NO:10, SEQ ID NO:11, SEQ ID NO:12, and SEQ ID NO:13, respectively.

```
Human THRAP1 3'UTR
                                        (SEQ ID NO: 6)
uucuugcuuu aaagcaauug gucuaaaaua uauguaaucg ucuuaauuaa aaaguugcag uaggguugc Chimp THRAP1 3'UTR
                                        (SEQ ID NO: 7)
uucuugcuuu aaagcaauug gucuaaaaua uauguaaucg ucuuaauuaa aacguugcag uaggguugc Mouse THRAP1 3'UTR
                                        (SEQ ID NO: 8)
uucuugcuuu aaagcaauug gucuaaaaua uauguaaucg ucuuaauuaa aacguugcag uaggguugc Rat THRAP1 3'UTR
                                        (SEQ ID NO: 9)
uucuugcuuu aaagcaauug gucuaaaaua uauguaaucg ucuuaauuaa aacguugcag uaggguugc Canine THRAP1 3'UTR
                                        (SEQ ID NO: 10)
uucuugcuuu aaagcaauug gucuaaaaua uauguaaucg ucuuaauuaa aacguugcag uaggguugc Chicken THRAP1 3'UTR
                                        (SEQ ID NO: 11)
uucuugcuuu aaagcaauug gucuaaaaua uauguaaucg ucuuaauuaa aacguugcag uaggguugc
```

```
Fugu THRAP1 3'UTR
                                                (SEQ ID NO: 12)
uuccugcuuu aagcaauugg uugaaaauau auguauguaa uggucuuaau uaaaaaaaca aacuaagaca aa Zebrafish THRAP1 3'UTR
                                                (SEQ ID NO: 13)
uuccugcuuu aaagcaauug gucuaaaaua uauguaaucg ucuucauuac aaaaacgaac caucaaacg
```

The present invention provides a method of treating cardiac fibrosis, cardiac hypertrophy or heart failure in a subject in need thereof comprising identifying a subject having cardiac fibrosis, cardiac hypertrophy or heart failure; and administering to the subject an agonist of miR-29 expression or function. The miR-29 agonist may be an agonist of miR-29a, miR-29b and/or miR-29c.

In one embodiment, agonists of miR-29a-c may be polynucleotides comprising the mature miR-29a-c sequence. In some embodiments, the polynucleotide comprises the sequence of SEQ ID NO: 18, SEQ ID NO: 19, or SEQ ID NO: 20. In another embodiment, the agonist of miR-29a-c may be a polynucleotide comprising the pri-miRNA or pre-miRNA sequence for miR-29a, miR-29b, and/or miR-29c. The polynucleotide comprising the mature miR-29a-c, pre-miR-29a-c, or pri-miR-29a-c sequence may be single stranded or double stranded. The polynucleotides may contain one or more chemical modifications, such as locked nucleic acids, peptide nucleic acids, sugar modifications, such as 2'-O-alkyl (e.g. 2'-β-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-29a-c sequence is conjugated to cholesterol. In another embodiment, the agonist of miR-29a-c may be an agent distinct from miR-29a-c that acts to increase, supplement, or replace the function of miR-29a-c.

In another embodiment, the agonist of miR-29a-c may be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-29a-c comprises a promoter "operably linked" to a polynucleotide encoding miR-29a, miR-29b, miR-29c, or combinations thereof. In another embodiment, the polynucleotide may encode the miR-29b-1/miR-29a cluster. In another embodiment, the polynucleotide may encode the miR-29b-2/miR-29c cluster. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding miR-29a-c may encode the primary-microRNA-29a-c sequence (pri-miR-29a-c), the precursor-microRNA-29a-c sequence (pre-miR-229a-c) or the mature miR-29a-c sequence. In another embodiment, the expression vector comprises a polynucleotide operably linked to a promoter, wherein said polynucleotide comprises the sequence of SEQ ID NO: 18. In another embodiment, the expression vector comprises a polynucleotide operably linked to a promoter, wherein said polynucleotide comprises the sequence of SEQ ID NO: 19. In still another embodiment, the expression vector comprises a polynucleotide operably linked to a promoter, wherein said polynucleotide comprises the sequence of SEQ ID NO: 20. The polynucleotide comprising the sequence of SEQ ID NO: 18, SEQ ID NO: 19, or SEQ ID NO: 20 may be about 18 to about 2000 nucleotides in length, about 70 to about 200 nucleotides in length, about 20 to about 50 nucleotides in length, or about 18 to about 25 nucleotides in length.

Throughout this application, the term "expression construct" is meant to include any type of genetic construct containing a nucleic acid coding for a gene product in which part or all of the nucleic acid encoding sequence is capable of being transcribed. Generally, the nucleic acid encoding a gene product is under transcriptional control of a promoter. A "promoter" refers to a DNA sequence recognized by the synthetic machinery of the cell, or introduced synthetic machinery, required to initiate the specific transcription of a gene.

The term promoter will be used here to refer to a group of transcriptional control modules that are clustered around the initiation site for a RNA polymerase. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter, RNA pol III promoter, and glyceraldehyde-3-phosphate dehydrogenase promoter can be used to obtain high-level expression of the polynucleotide of interest. The use of other viral or mammalian cellular or bacterial phage promoters which are well-known in the art to achieve expression of a polynucleotide of interest is contemplated as well, provided that the levels of expression are sufficient for a given purpose.

By employing a promoter with well-known properties, the level and pattern of expression of the polynucleotide of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct. In a preferred embodiment, the polynucleotide encoding the miR-29a-c or miR-29a-c antagonist is operably-linked to a fibroblast specific promoter.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |

TABLE 1-continued

Promoter and/or Enhancer

| Promoter/Enhancer | References |
|---|---|
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) | Palmiter et al., 1982; Haslinger et al., 1985; |
|  | Heavy metals | Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing the polynucleotides of the invention in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to affect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kasp a et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

In some embodiments of the invention, it is desirable to inhibit the expression or activity of miR-29a-c to increase collagen deposition. For example, in one embodiment, the invention provides a method of inducing collagen deposition in a tissue comprising contacting said tissue with an antagonist of miR-29a-c. The antagonist or inhibitor of miR-29a-c function may be directed at miR-29a, miR-29b and/or at miR-29c.

The function of miRNAs may be inhibited by the administration of antagomirs. Initially described by Kriitzfeldt and colleagues (Kriitzfeldt et al., 2005), "antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

In one embodiment, the antagonist of miR-29a-c is an antagomir. The antagomir may comprise a sequence that is at least partially complementary to the mature miRNA sequence of miR-29a, miR-29b, or miR-29c. In another embodiment, the antagomir comprises a sequence that is at least partially complementary to the sequence of SEQ ID NO: 18, SEQ ID NO: 19, or SEQ ID NO: 20. In another embodiment, the antagomir comprises a sequence that is 100% complementary to SEQ ID NO: 18, SEQ ID NO: 19, or SEQ ID NO: 20.

Inhibition of microRNA function may also be achieved by administering antisense oligonucleotides targeting the mature miR-29a, miR-29b or miR-29c sequences. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Preferable antisense oligonucleotides useful for inhibiting the activity of microRNAs are about 19 to about 25 nucleotides in length. Antisense oligonucleotides may comprise a sequence that is at least partially complementary to a mature miRNA sequence, e.g. at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

In another embodiment of the invention, the antagonist of miR-29a-c is a chemically-modified antisense oligonucleotide. The chemically-modified antisense oligonucleotide may comprise a sequence that is at least partially complementary to the mature miRNA sequence of miR-29a, miR-29b, or miR-29c. In yet another embodiment, the chemically-modified antisense oligonucleotide comprises a sequence that is at least partially complementary to the sequence of SEQ ID NO: 18, SEQ ID NO: 19, or SEQ ID NO: 20. In another embodiment, the chemically-modified antisense oligonucleotide comprises a sequence that is 100% complementary to SEQ ID NO: 18, SEQ ID NO: 19, or SEQ ID NO: 20.

Antisense oligonucleotides may comprise a sequence that is substantially complementary to a precursor miRNA sequence (pre-miRNA) for miR-29a-c. In some embodiments, the antisense oligonucleotide comprises a sequence that is substantially complementary to a sequence located outside the stem-loop region of the pre-miR-29a, pre-miR-29b, or pre-miR-29c sequence.

Another approach for inhibiting the function of miR-29a-c is administering an inhibitory RNA molecule having at least partial sequence identity to the mature miR-29a, miR-29b and miR-29c sequences. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical, e.g. about 75%, 80%, 85%, 90%, 95%, 96%, 97%, 98%, or 99% identical, to the mature miRNA sequence. In some embodiments, the double-stranded regions of the inhibitory RNA comprise a sequence that is at least substantially identical to the mature miRNA sequence. "Substantially identical" refers to a sequence that is about 95%, 96%, 97%, 98%, or 99% identical to a target polynucleotide sequence. In other embodiments, the double-stranded regions of the inhibitory RNA molecule may be 100% identical to the target miRNA sequence.

In one embodiment, an antagonist of miR-29a-c is an inhibitory RNA molecule comprising a double-stranded region, wherein the double-stranded region comprises a sequence having 100% identity to the mature miR-29a (SEQ ID NO: 18), miR-29b (SEQ ID NO: 19), or miR-29c (SEQ ID NO: 20) sequence. In some embodiments, antagonists of miR-29a-c are inhibitory RNA molecules which comprise a double-stranded region, wherein said double-stranded region comprises a sequence of at least about 75%, 80%, 85%, 90%, 95%, 96%, 97%, 98%, or 99% identity to the mature miR-29a, miR-29b, or miR-29c sequence.

In another embodiment, an inhibitory RNA molecule may be a ribozyme. A ribozyme is a catalytic RNA that hydrolyzes phosphodiester bonds of RNA molecules. The ribozyme may be designed to target one or more of miR-29a, miR-29b, and miR-29c resulting in their hydrolysis.

In certain embodiments, expression vectors are employed to express an antagonist of miR-29a-c (e.g., antagomirs, antisense oligonucleotides, and inhibitory RNA molecules). In one embodiment, an expression vector for expressing an antagonist of miR-29a-c comprises a promoter operably linked to a polynucleotide encoding an antisense oligonucleotide, wherein the sequence of the expressed antisense oligonucleotide is at least partially complementary to the mature miR-29a, miR-29b, or miR-29c sequence. In yet another embodiment, an expression vector for expressing an inhibitor of miR-29a-c comprises one or more promoters operably linked to a polynucleotide encoding a shRNA or siRNA, wherein the expressed shRNA or siRNA comprises a sequence that is identical, partially identical, or substantially identical to the mature miR-29a, miR-29b, or miR-29c sequence. "Partially identical" refers to a sequence that is at least about 75%, 80%, 85%, 90%, 95%, 96%, 97%, 98%, or 99% identical to a target polynucleotide sequence. "Substantially identical" refers to a sequence that is at least about 95%, 96%, 97%, 98%, or 99% identical to a target polynucleotide sequence.

Current medical management of cardiac hypertrophy in the setting of a cardiovascular disorder includes the use of at least two types of drugs inhibitors of the renin-angiotensin system, and β-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide Y antagonists (WO 98/33791). Despite currently available pharmaceutical compounds, prevention and treatment of cardiac hypertrophy, and subsequent heart failure, continue to present a therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

The present invention provides a method of treating cardiac fibrosis, cardiac hypertrophy or heart failure in a subject in need thereof comprising identifying a subject having cardiac fibrosis, cardiac hypertrophy or heart failure; and administering to the subject an agonist of miR-29 expression or function. Preferably, administration of a miR-29 agonist results in the improvement of one or more symptoms of pathologic cardiac fibrosis, hypertrophy or heart failure in the subject, or in the delay in the transition from cardiac hypertrophy to heart failure. The one or more improved symptoms may be increased exercise capacity, increased cardiac ejection volume, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease related morbidity or mortality. In addition, use of agonists of miR-29a-c may prevent cardiac hypertrophy and its associated symptoms from arising either directly or indirectly.

In another embodiment, there is provided a method of preventing pathologic hypertrophy or heart failure in a subject in need thereof comprising identifying a subject at risk of developing pathologic cardiac hypertrophy or heart failure; and promoting the expression or activity of miR-29a-c in cardiac cells of the subject. Cardiac cells include cardiac myocytes, fibroblasts, smooth muscle cells, endothelial cells, and any other cell type normally found in cardiac tissue. The miR-29a-c agonist may be an agonist of miR-29a, miR-29b and/or miR-29c. The subject at risk may exhibit one or more of a list of risk factors comprising cardiac fibrosis, low expression of miR-29, long-standing uncontrolled hypertension, uncorrected valvular disease, chronic angina, recent myocardial infarction, congenital predisposition to heart disease and/or pathological hypertrophy, and/or may be diagnosed as having a genetic predisposition to cardiac hypertrophy, and/or may have a familial history of cardiac hypertrophy.

In another embodiment, there is provided a method of treating myocardial infarction in a subject in need thereof comprising promoting expression or activity of miR-29a-c in cardiac cells of the subject. In another embodiment, the invention provides a method of preventing cardiac hypertrophy and dilated cardiomyopathy in a subject in need thereof comprising promoting expression or activity of miR-29a-c in cardiac cells of the subject. In another embodiment, the invention provides a method of inhibiting progression of cardiac hypertrophy in a subject in need thereof comprising promoting expression or activity of miR-29a-c in cardiac cells of the subject. Another embodiment is a method of increasing exercise tolerance in a subject with heart failure or cardiac hypertrophy comprising promoting expression or activity of miR-29a-c in cardiac cells of the subject. Another embodiment is a method of reducing hospitalization in a subject with heart failure or cardiac hypertrophy comprising promoting expression or activity of miR-29a-c in cardiac cells of the subject. In some embodiments, the invention provides methods for improving quality of life and decreasing morbidity or mortality in a subject with heart failure or cardiac hypertrophy comprising promoting expression or activity of miR-29a-c in cardiac cells of the subject.

Treatment regimens would vary depending on the clinical situation. However, long-term maintenance would appear to be appropriate in most circumstances. It also may be desirable to treat hypertrophy with agonists of miR-29a-c intermittently, such as within a brief window during disease progression.

In addition, the miR-29 family is involved in the regulation of cardiac fibrosis. Since this miR family is enriched in fibroblasts compared to myocytes, it is likely that myocytes secrete a factor, possibly BNP, which upregulates the miR-29 family in fibroblast cells and thus protects against the development of cardiac fibrosis. This factor is very high in miR-208 KO mice, which correlates with the upregulation of miR-29a-c and repression of fibrosis. miR-29a-c levels are elevated in normal heart disease, which is likely a protective effect to limit collagen deposition. Thus, the particular use of miR-29a-c and agonists thereof in repressing cardiac fibrosis and collagen deposition in cardiac tissues is contemplated. A comparable mechanism for the activation of the miR-29 family may be applicable in skeletal muscle fibrosis as well. miR-29a-c regulates the expression of a number of extracellular matrix genes, such as fibrillin 1 (FBN1), collagen type I, α1 (COL1A1), collagen type I α2 (COL1A2), and collagen type III, α1 (COL3A1) (see Example 4). Accordingly, the present invention also provides methods of regulating one or more extracellular matrix genes in a cell.

In one embodiment, the method comprises contacting the cell with an agonist of miR-29 a-c. In another embodiment, the method comprises contacting the cell with an antagonist of miR-29a-c. In still another embodiment, the one or more extracellular matrix genes include fibrillin 1 (FBN1), collagen type I, α1 (COL1A1), collagen type I α2 (COL1A2), and collagen type III, α1 (COL3A1). In some embodiments, the one or more extracellular matrix genes are upregulated following contact of the cell with an antagonist of miR-29a-c. In other embodiments, the one or more extracellular matrix genes are downregulated following contact of the cell with an agonist of miR-29a-c.

The inventors have demonstrated that miR-29a-c expression was decreased in cardiac fibroblasts exposed to TGFβ, suggesting that the decrease in miR-29a-c following myocardial infarction might be TGFβ-regulated (Example 5). Interestingly, natriuretic peptides like B-type natriuretic peptide (BNP) have been shown to inhibit TGFβ-regulated gene expression related to fibrosis and myofibroblast conversion (Kapoun et al., 2004). In this regard, the inventors reported previously that mice lacking the cardiac-specific miRNA miR-208 were resistant to cardiac fibrosis and remodeling and exhibited increased expression of BNP at baseline (van Rooij et al., 2007). Since BNP is known to antagonize the effects of TGFβ, the inventors suggest that the increased levels of BNP in these mice might enhance the expression of miR-29a-c. Indeed, a dose-dependent increase in miR-29a-c expression was observed upon removal of miR-208, which coincided with an increasing expression level of BNP (Example 5). These data indicate that TGFβ induces the expression of collagen related genes in fibroblasts at least partly through decreasing the level of miR-29a-c, which can be inhibited by BNP secreted by cardiomyocytes. Thus, the present invention provides a method of increasing miR-29a-c expression and/or activity in a subject by administering at least one TGFβ inhibitor. TGFβ inhibitors may include anti-TGFβ antibodies, TGFβ antisense molecules, and small molecules that inhibit TGFβ activity as described in U.S. Pat. No. 6,509,318, which is herein incorporated by reference in its entirety. TGFβ inhibitors may also be used in conjunction with miR-29a-c agonists as a combination therapy to treat cardiac fibrosis, cardiac hypertrophy, or heart failure in a subject. TGFβ inhibitors may also be co-administered with miR-29a-c agonists to treat or prevent tissue fibrosis in a subject.

In addition to playing an important role in controlling fibrosis in the heart, the ubiquitous expression of the miR-29 family suggests that it also may play a role in other fibrotic indications, such as those involving the kidney, liver and lungs. Fibrosis is also observed secondary to diabetes. Type 1 and type 2 diabetic patients are at increased risk of cardiomyopathy. Cardiomyopathy in diabetes is associated with a cluster of features, including decreased diastolic compliance, interstitial fibrosis, and myocyte hypertrophy.

The present invention also provides a method of treating or preventing a tissue fibrosis in a subject. In one embodiment, the method comprises identifying a subject having or at risk of tissue fibrosis; and increasing the expression and/or activity of miR-29a-c in skeletal muscle or fibroblast cells of the subject. In another embodiment, the tissue fibrosis is cardiac fibrosis, scleroderma (localized or systemic), skeletal muscle fibrosis, hepatic fibrosis, kidney fibrosis, pulmonary fibrosis, or diabetic fibrosis. In some embodiments, increasing the expression and/or activity of miR-29a-c comprises administering an agonist of miR-29a-c to the subject. In other embodiments, increasing the expression and/or activity of miR-29a-c comprises administering to the subject an expression vector that encodes miR-29a-c. In another embodiment, the method further comprises administering to the subject a non-miR-29a-c fibrotic therapy.

The present invention encompasses methods of treating tissue fibrosis associated with one or more conditions or disorders in a subject in need thereof. In one embodiment, the method comprises administering to the subject an agonist of miR-29a-c. In another embodiment, the method comprises administering to the subject an expression vector that encodes miR-29a-c. The one or more conditions or disorders associated with tissue fibrosis may include, but are not limited to, congenital hepatic fibrosis (CHF); renal tubulointerstitial fibrosis; pulmonary fibrosis associated with an autoimmune disorder (e.g. rheumatoid arthritis, lupus and sarcoidosis); interstitial fibrosis associated with diabetic cardiomyopathy; skeletal muscle fibrosis associated with muscular dystrophies (e.g. Becker muscular dystrophy and Duchenne muscular dystrophy), denervation atrophies, and neuromuscular diseases (e.g. acute polyneuritis, poliomyelitis, Werdig/Hoffman disease, amyotrophic lateral sclerosis, and progressive bulbar atrophy disease).

The present invention also contemplates methods of treating pathologies/deficiencies that are characterized by the loss, lack, or underproduction of collagen. Using an antagonist of miR-29a-c, the expression of collagen can be increased to replace missing collagen or supplement existing collagen where there is a need. Thus, the present invention provides a method of inducing collagen deposition in a tissue comprising contacting said tissue with an antagonist of miR-29a-c. The antagonist may be directed at miR-29a, miR-29b and/or at miR-29c. In one embodiment, the antagonist comprises a sequence that is complementary to SEQ ID NO: 18. In another embodiment, the antagonist comprises a sequence that is complementary to SEQ ID NO: 19. In another embodiment, the antagonist comprises a sequence that is complementary to SEQ ID NO: 20. The antagonist may be an antagomir of miR-29a-c, an antisense oligonucleotide that targets a mature miR-29a-c sequence, or an inhibitory RNA molecule, such as a siRNA or a shRNA, that comprises a sequence identical to a mature miR-29a-c sequence, a ribozyme or any other inhibitory nucleic acid. The antagonist may be linked or conjugated to agents that facilitate the entry of the antagonist into cells or tissues. Various conditions and disorders in which an increase in collagen deposition would be beneficial and can be treated by administering an antagonist of miR-29a-c include, but are not limited to, Ehlers-Danlos syndrome (EDS); Vitamin C deficiency (a.k.a scurvy); aging of the skin (e.g. natural aging and photoaging due to sun damage); and stretch marks (striae).

Ehlers-Danlos syndrome (EDS) is a group of rare genetic disorders affecting humans and domestic animals caused by a defect in collagen synthesis. Depending on the individual mutation, the severity of the disease can vary from mild to life-threatening. Mutations in the ADAMTS2, COL1A1, COL1A2, COL3A1, COL5A1, COL5A2, PLOD1 and TNXB genes cause EDS. Mutations in these genes usually alter the structure, production, or processing of collagen or proteins that interact with collagen. A defect in collagen can weaken connective tissue in the skin, bones, blood vessels, and organs, resulting in the features of the disorder. Thus, collagen deposition induced by miR-29a-c antagonists of the invention would act to replenish the level of normal collagen in EDS patients and alleviate symptoms of the disease. Similarly, administration of an antagonist of miR-29a-c would benefit subjects suffering from vitamin C deficiency or scurvy. Vitamin C deficiency is a disease that results from insufficient intake of vitamin C, which is required for normal collagen synthesis in humans.

Collagen deposition in tissues resulting from the administration of an antagonist of miR-29a-c would also be useful in various cosmetic applications. Effects of aging of the skin produced by natural aging processes or photodamage resulting from over-exposure to the sun could be reduced by administering to a subject in need thereof a miR-29a-c antagonist. Administration of miR-29a-c antagonists may also facilitate the disappearance of stretch marks. Stretch marks are a form of scarring on the skin that are caused by tearing of the dermis. Stretch marks are the result of the rapid stretching of the skin associated with rapid growth (common in puberty) or weight gain (e.g., pregnancy).

The tissue to which the inventive methods may be applied include facial tissue, such a forehead tissue, a lip, a cheek, a chin, an eyebrow, an eyelid, under the eye, or near the mouth, hand tissue, neck tissue, arm tissue, leg tissue, stomach tissue or breast tissue. In some embodiments, the tissue may comprise a wound, a skin graft, scar tissue, wrinkles, lax skin, sun damage, chemical damage, heat damage, cold damage, and/or stretch marks.

In another embodiment of the invention, the contacting of the tissue with the miR-29a-c antagonist comprises injection into said tissue, injection into vasculature that feeds said tissue, or topical application. The topical application may be an ointment, cream, gel, salve, or balm. In another embodiment, the method further comprises use of a pressure bandage or dressing. The antagonist of miR-29a-c may be contacted with said tissue more than once. In some embodiments, the antagonist is contacted with said tissue 2, 3, 4, 5, 6, 7, 8, 9, 10, 15, 20, 25, 30, 35, 40, 45, 50, 60, 70, 80, 90 or 100 times. In other embodiments, the antagonist is contacted with said tissue over 2, 3, 4, 5, or 6 days, 1, 2, 3, or 4 weeks, 1, 2, 3, 4, 5, 6, 7, 8, 9, or 11 months, or 1, 2, 3, 3, 4, 5, 6, 7, 8, 9, 10, 15, 20, or 25 years.

In still another embodiment, the method further comprises contacting said tissue with a second agent. The second agent may include, but is not limited to, topical vitamin A, topical vitamin C, or vitamin E. In another embodiment, the method further comprises subjecting said tissue to a second treatment. The second treatment may comprise a chemical peel, laser treatment, dermaplaning, or dermabrasion. In another embodiment, the tissue is in a subject that suffers from Ehler's-Danlos syndrome or Vitamin C deficiency.

The present invention also contemplates the use of miR-29a-c antagonists as profibrotic agents to convert soft plaques in the vasculature into fibrotic tissue to prevent myocardial infarction. Soft plaques are a build-up of lipids containing predominantly cholesterol that lie underneath the endothelial lining of the arterial wall. Recently, it was recognized that these soft plaques are prone to rupture resulting in the formation of a blood clot, which can potentially block blood flow through the artery and cause a heart attack (i.e. myocardial infarction). It is these soft plaques that are often responsible in causing a healthy subject with no symptoms to suffer a seemingly unexpected heart attack. After a soft plaque ruptures, the vessel wall heals and the soft plaque becomes a hard plaque, which rarely cause further problems. Thus, strategies for converting soft plaques into fibrotic tissue would prevent the soft plaques from rupturing and possibly inducing a myocardial infarction.

As described in detail above, inhibition of miR-29a-c leads to an increase in collagen deposition and the formation of fibrotic tissue. Accordingly, the present invention provides a method for increasing fibrotic tissue formation in the wall of a vessel comprising delivering an antagonist of miR-29a-c to one or more soft plaque sites in the vessel wall, wherein the soft plaque is converted to fibrotic tissue following delivery of the antagonist of miR-29a-c. Soft plaques can be identified by methods known in the art, including, but not limited to, intravascular ultrasound and computed tomography (Sahara et al. (2004) European Heart Journal, Vol. 25: 2026-2033; Budhoff (2006) J. Am. Coll. Cardiol., Vol. 48: 319-321; Hausleiter et al. (2006) J. Am. Coll. Cardiol., Vol. 48: 312-318). Any of the miR-29a-c antagonists described herein are suitable for use in the method.

The miR-29a-c antagonist may delivered to the one or more soft plaque sites by direct injection or by using a catheter or a device that isolates the coronary circulation. In one embodiment, the miR-29a-c antagonist is delivered to the one or more soft plaque sites by a medical device used in vascular surgery, such as a stent or balloon. The miR-29 antagonist may be coated on a metal stent to form a drug-eluting stent. A drug-eluting stent is a scaffold that holds open narrowed or diseased arteries and releases a compound to prevent cellular proliferation and/or inflammation. miR-29a-c antagonists may be applied to a metal stent imbedded in a thin polymer for release of the miR-29a-c over time. Methods of coating stents with therapeutic compounds are known in the art. See, e.g., U.S. Pat. No. 7,144,422; U.S. Pat. No. 7,055,237; and WO 2004/004602, which are here incorporated by reference in their entireties. In some embodiments, the miR-29a-c may be used in combination with other anti-restenosis compounds to produce a formulation for incorporation into drug-eluting stents and balloons. Suitable compounds for use in combination with the antagonists of miR-29a-c include, but are not limited to, paclitaxel, rapamycin (sirolimus), tacrolimus, zotarolimus, everolimus, docetaxel, pimecrolimus, and derivatives thereof.

The present invention also contemplates methods for scavenging or clearing a miR-29a-c agonist following treatment. In one embodiment, the method comprises overexpression of binding site regions for miR-29a-c in fibroblasts using a fibroblast specific promoter. The binding site regions preferably contain a sequence of the seed region for miR-29a-c. In some embodiments, the binding site may contain a sequence from the 3'UTR of one or more targets of miR-29a-c, such as COL1A1, COL1A2, COL1A3 and/or FBN1. In another embodiment, a miR-29a-c antagonist may be administered after a miR-29a-c agonist to attenuate or stop the function of the microRNA. In another embodiment, the present invention provides a method for scavenging or clearing miR-29a-c antagonists following treatment. The method may comprise overexpressing binding sites for the miR-20a-c antagonists in fibroblasts or other tissue in which a miR-29a-c antagonist was administered.

Combined Therapy

In another embodiment, it is envisioned to use an agonist of miR-29a-c in combination with other therapeutic modalities for treating cardiac hypertrophy, heart failure and myocardial infarction. Thus, one may also provide to the subject more "standard" pharmaceutical cardiac therapies in combination with the miR-29a-c agonist. Examples of other therapies include, without limitation, so-called "beta blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes an agonist of miR-29a-c and a standard pharmaceutical agent, or by contacting the cell with two distinct compositions or formulations, at the same time, wherein one composition includes an agonist of miR-29a-c and the other includes the standard pharmaceutical agent. Alternatively, the therapy using an agonist of miR-29a-c may precede or follow administration of the other agent(s) by intervals ranging from minutes to weeks. In embodiments where the standard pharmaceutical agent and miR-29a-c agonist are applied separately to the cell, one would generally ensure that a significant period of time did not expire between the time of each delivery, such that the pharmaceutical agent and miR-29a-c agonist would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an agonist of miR-29a-c, or the other pharmaceutical agent will be desired. In this regard, various combinations may be employed. By way of illustration, where the agonist of miR-29a-c is "A" and the other agent is "B," the following permutations based on 3 and 4 total administrations are exemplary:

| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated.

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain embodiments, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

Non-limiting examples of resins/bile acid sequesterants include cholestyramine (cholybar, questran), colestipol (colestid) and polidexide.

Non-limiting examples of HMG CoA reductase inhibitors include lovastatin (mevacor), pravastatin (pravochol) or simvastatin (zocor).

Non-limiting examples of nicotinic acid derivatives include nicotinate, acepimox, niceritrol, nicoclonate, nicomol and oxiniacic acid.

Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin. Non-limiting examples of an antiarteriosclerotic include pyridinol carbamate.

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain embodiments, antithrombotic agents that can be administered orally, such as, for example, aspirin and wafarin (coumadin), are preferred.

Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane) and ticlopidine (ticlid).

Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a subject is suffering from a hemorrhage or an increased likelihood of hemorrhaging, an agent that may enhance blood coagulation may be used. Non-limiting examples of a blood coagulation promoting agents include thrombolytic agent antagonists and anticoagulant antagonists.

Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Non-limiting examples of a β-blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of an agent that prolong repolarization, also known as a Class III antiarrhythmic agent, include amiodarone (cordarone) and sotalol (betapace).

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhythmic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an α-blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

In certain embodiments, an antihypertensive agent is both an α- and β-adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotensin II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, troInitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Non-limiting examples of arylethanolamine derivatives include amosulalol, bufuralol, dilevalol, labetalol, pronethalol, sotalol and sulfinalol.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Non-limiting examples of dihydropyridine derivatives include amlodipine, felodipine, isradipine, nicardipine, nifedipine, nilvadipine, nisoldipine and nitrendipine.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Non-limiting examples of hydrazines/phthalazines include budralazine, cadralazine, dihydralazine, endralazine, hydracarbazine, hydralazine, pheniprazine, pildralazine and todralazine.

Non-limiting examples of imidazole derivatives include clonidine, lofexidine, phentolamine, tiamenidine and tolonidine.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Non-limiting examples of reserpine derivatives include bietaserpine, deserpidine, rescinnamine, reserpine and syrosingopine.

Non-limiting examples of sulfonamide derivatives include ambuside, clopamide, furosemide, indapamide, quinethazone, tripamide and xipamide.

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Non-limiting examples of agents for the treatment of congestive heart failure include anti-angiotensin II agents, afterload-preload reduction treatment, diuretics and inotropic agents.

In certain embodiments, an animal subject that can not tolerate an angiotensin antagonist may be treated with a combination therapy. Such therapy may combine administration of hydralazine (apresoline) and isosorbide dinitrate (isordil, sorbitrate).

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, aminosometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

In certain embodiments, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Drug Formulations and Routes for Administration to Subjects

The present invention also provides a pharmaceutical composition comprising an agonist or antagonist of miR-29a-c. The agonist may be an expression vector comprising a nucleic acid segment encoding miR-29a-c, or a polynucleotide comprising a mature miR-29a-c sequence or an effective portion thereof. The agonist may be comprised in a lipid delivery vehicle. The antagonist may be a polynucleotide that hybridizes to miR-29a-c or a target thereof.

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors (e.g. antagonists) of microRNA function or constructs expressing particular microRNAs. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a subject. Aqueous compositions of the present invention comprise an effective amount of the delivery vehicle comprising the inhibitor polynucleotides or miRNA polynucleotide sequences (e.g. liposomes or other complexes or expression vectors) or cells, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA antagonists or expression constructs comprising miRNA sequences may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Cosmetic formulations for increasing collagen deposition in tissues may comprise at least one antagonist of miR-29a-c. The antagonist may be an antagonist of miR-29a, miR-29b, miR-29c, or combinations thereof. In some embodiments, the antagonist of miR-29a-c is an antagomir. The antagonist may be linked or conjugated to agents that facilitate the entry of the antagonist into cell or tissues. Such agents may include cell internalization transporters, such as antennapedia, TAT, Buforin II, Transportan, model amphipathic peptide, K-FGF, Ku70, Prion, pVEC, Pep-1, SynB1, SynB3, SynB5, Pep-7, HN-1, Bis-Guanidinium-Spermidine-Cholesterol, Bis-Guanidinium-Tren-Cholesterol, and polyarginine. The agent may be linked to the miR-29a-c antagonist at its amino or carboxy terminus. In one embodiment, the agent is linked to the antagonist by a sequence that is cleaved upon entry to the cell. Such sequences typically comprise consensus sequences for proteases as are known in the art.

The cosmetic compositions can be formulated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain embodiments, the concentrations and combinations of the ingredients are selected in such a way that the combinations are chemically compatible and do not form complexes which precipitate from the finished product.

It is also contemplated that aromatic skin-active ingredients and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. No. 6,387,398; U.S. Pat. No. 6,203,802; U.S. Pat. No. 5,411,744; and Kreuter 1998, which are herein incorporated by reference in their entireties).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation.

The compositions of the present invention can be incorporated into products. Non-limiting examples of products include cosmetic products, food-based products, pharmaceutical products, etc. By way of example only, non-limiting cosmetic products include sunscreen products, sunless skin tanning products, hair products, fingernail products, moisturizing creams, skin benefit creams and lotions, softeners, day lotions, gels, ointments, foundations, night creams, lipsticks, mascaras, eyeshadows, eyeliners, cheek colors, cleansers, toners, masks, or other known cosmetic products or applications. Additionally, the cosmetic products can be formulated as leave-on or rinse-off products.

Compositions of the present invention can include additional ingredients. Non-limiting examples of additional ingredients include cosmetic ingredients (both active and non-active) and pharmaceutical ingredients (both active and non-active). The CTFA International Cosmetic Ingredient Dictionary and Handbook (2004) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes).

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

Any of the compositions described herein may be comprised in a kit. In a non-limiting example, an individual miRNA is included in a kit. The kit may further include water and hybridization buffer to facilitate hybridization of the two strands of the miRNAs. In some embodiments, the kit may include one or more oligonucleotides for inhibiting the function of a target miRNA. The kit may also include one or more transfection reagent(s) to facilitate delivery of the miRNA or miRNA antagonists to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or miRNA inhibitory oligonucleotides or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA agonist or antagonist by various administration routes, such as parenteral or catheter administration.

It is contemplated that such reagents are embodiments of kits of the invention. Such kits, however, are not limited to the particular items identified above and may include any reagent used for the manipulation or characterization of miRNA.

Methods for Identifying Modulators

The present invention further comprises methods for identifying agonists of miR-29a-c that are useful in the prevention or treatment or reversal of cardiac fibrosis, cardiac hypertrophy or heart failure. These assays may comprise random screening of large libraries of candidate compounds; alternatively, the assays may be used to focus on particular classes of compounds selected with an eye towards structural attributes that are believed to make them more likely to promote the expression and/or function of miR-29a-c.

To identify a modulator of miR-29a-c, one generally will determine the function of a miR-29a-c in the presence and absence of the candidate compound. For example, a method generally comprises:

(a) providing a candidate compound;
(b) admixing the candidate compound with a miR-29;
(c) measuring miR-29a-c activity; and
(d) comparing the activity in step (c) with the activity of miR-29a-c in the absence of the candidate compound, wherein a difference between the measured activities of miR-29a-c indicates that the candidate compound is, indeed, a modulator of miR-29a-c.

Assays also may be conducted in isolated cells, organs, or in living organisms.

It will, of course, be understood that all the screening methods of the present invention are useful in themselves notwithstanding the fact that effective candidates may not be found.

The invention provides methods for screening for such candidates, not solely methods of finding them.

As used herein the term "candidate compound" refers to any molecule that may potentially modulate fibrosis- or collagen-regulating aspects of miR-29a-c. One will typically acquire, from various commercial sources, molecular libraries that are believed to meet the basic criteria for useful drugs in an effort to "brute force" the identification of useful compounds. Screening of such libraries, including combinatorially-generated libraries (e.g., antagomir libraries), is a rapid and efficient way to screen a large number of related (and unrelated) compounds for activity. Combinatorial approaches also lend themselves to rapid evolution of potential drugs by the creation of second, third, and fourth generation compounds modeled on active, but otherwise undesirable compounds.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564, which is herein incorporated by reference in its entirety. Large numbers of small antagomir compounds may be synthesized on a solid substrate, such as plastic pins or some other surface. Such molecules can be rapidly screening for their ability to inhibit miR-29a-c.

The present invention also contemplates the screening of compounds for their ability to modulate miR-29a-c activity and expression in cells. Various cell lines, including those derived from skeletal muscle cells, can be utilized for such screening assays, including cells specifically engineered for this purpose. Primary cardiac cells also may be used, as can the H9C2 cell line.

In vivo assays involve the use of various animal models of heart disease, musculoskeletal disease, fibrosis, or collagen-loss including transgenic animals, that have been engineered to have specific defects, or carry markers that can be used to measure the ability of a candidate substance to reach and affect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of hypertrophic signaling pathways and physical symptoms of hypertrophy. Also, measuring toxicity and dose responses can be performed in animals in a more meaningful fashion than in in vitro or in cyto assays.

Transgenic Animals

A particular embodiment of the present invention provides transgenic animals that lack one or both functional alleles of miR-29a, miR-29b, and/or miR-29c. Also, transgenic animals that express miR-29a-c under the control of an inducible, tissue selective or a constitutive promoter, recombinant cell lines derived from such animals, and transgenic embryos may be useful in determining the exact role that miR-29a-c plays in the control of fibrosis and in the development of pathologic cardiac hypertrophy and heart failure. Furthermore, these transgenic animals may provide an insight into heart development. The use of an inducible or repressable miR-29a-c encoding nucleic acid provides a model for over- or unregulated expression. Also, transgenic animals that are "knocked out" for miR-29a-c, in one or both alleles, are contemplated. Also, transgenic animals that are "knocked out" for miR-29a-c, in one or both alleles for one or both clusters, are contemplated.

In a general embodiment, a transgenic animal is produced by the integration of a given transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in in Palmiter et al. (1982); and in Sambrook et al. (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by C02 asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

DEFINITIONS

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor subtype (generally ($β_1$); such antagonists are termed "$β_1$-specific adrenergic receptor antagonists" and "$β_2$-specific adrenergic receptor antagonists." The term β-adrenergic receptor antagonist" refers to chemical compounds that are selective and non-selective antagonists.

Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the renin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quiapril and ramipril. The use of derivatives of known ACE inhibitors is encompassed by the methods of the present invention. Indeed any compound, which functionally behaves as an ACE inhibitor, is encompassed by the methods of the present invention.

As used herein, the term "genotypes" refers to the actual genetic make-up of an organism, while "phenotype" refers to physical traits displayed by an individual. In addition, the "phenotype" is the result of selective expression of the genome (i.e., it is an expression of the cell history and its response to the extracellular environment). Indeed, the human genome contains an estimated 30,000-35,000 genes. In each cell type, only a small (i.e., 10-15%) fraction of these genes are expressed.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Although section headers have been inserted into this application to facilitate review, such headers should not be construed as a division of embodiments.

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Encoded within an intron of the α-MHC gene is miR-208 (FIG. 1A). Like α-MHC, miR-208 is expressed specifically in the heart with trace expression in the lung (FIG. 1B). miR-208 is processed out of the α-MHC pre-mRNA rather than being transcribed as a separate transcript. Intriguingly, however, miR-208 displays a remarkably long half-life of at least 14 days, and can thereby exert functions even when α-MHC mRNA expression has been down-regulated. Although genetic deletion of miR-208 in mice failed to induce an overt phenotype, microarray analysis on hearts from wild-type and miR-208$^{-/-}$ animals at 2 months of age revealed removal of miR-208 to result in pronounced expression of numerous fast skeletal muscle contractile protein genes, which are normally not expressed in the heart. Thus, these results suggest that under normal conditions miR-208 is co-expressed with the sole cardiac-specific MHC gene to maintain cardiomyocyte identity by repressing the expression of skeletal muscle genes in the heart.

Figure 5:
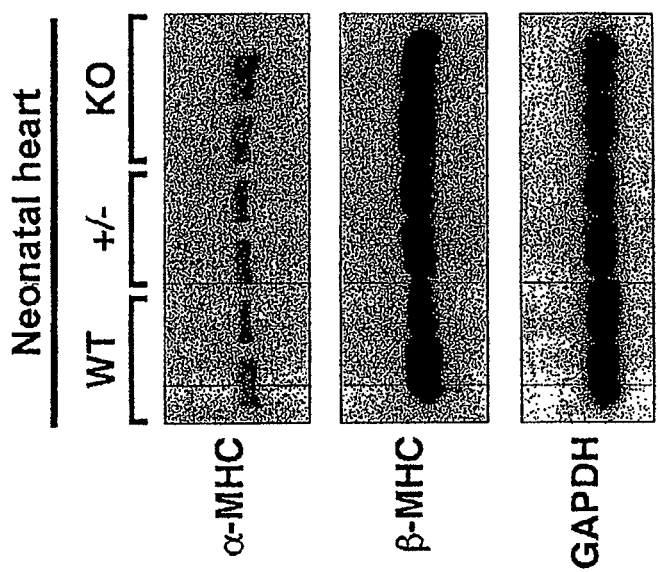
FIG. 5. Western analysis of α-MHC and β-MHC protein levels in hearts of neonatal mice of the indicated genotypes. Two mice of each genotype were analyzed. GAPDH was detected as a loading control.
Figure 6:
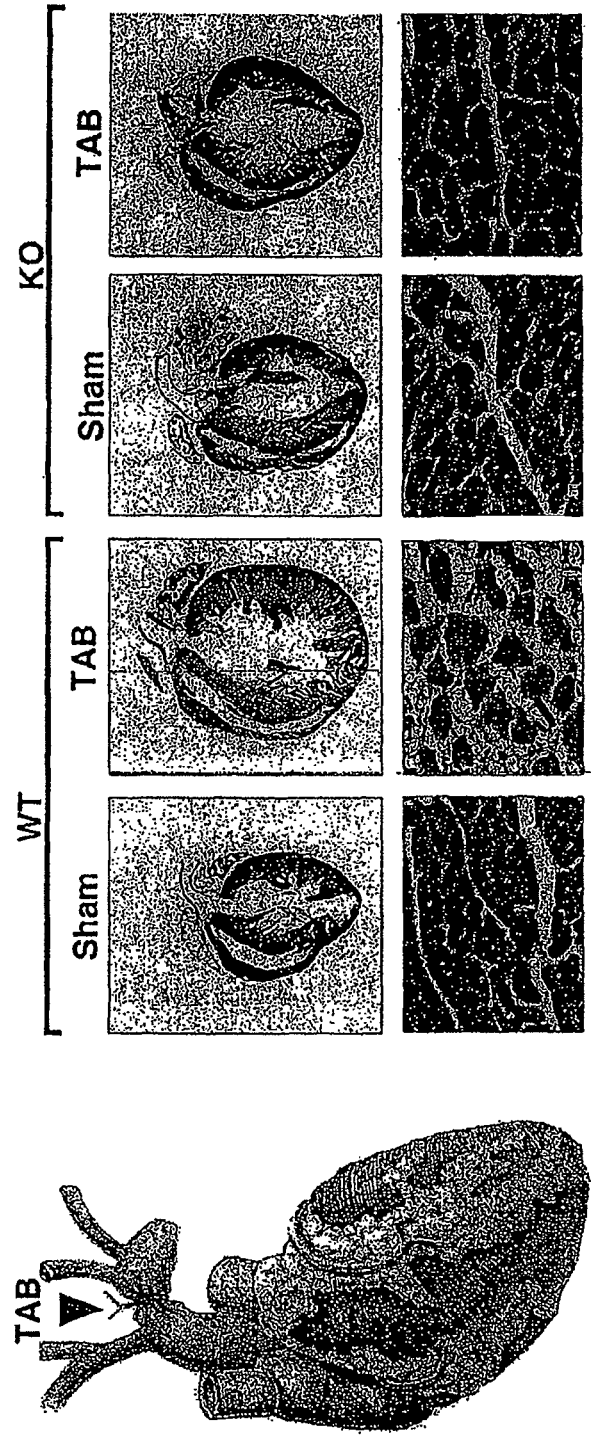
FIG. 6. MiR-208$^{-/-}$ mice show reduced cardiac hypertrophy in response to pressure overload. Histological sections of hearts of wild-type and miR-208$^{-/-}$ mice stained for Masson trichrome. The absence of miR-208 diminishes hypertrophy and fibrosis seen in wild-type mice subjected to thoracic aortic banding (TAB) for 21 days. Scale bar equals 2 mm in top panel and 20 μm for bottom panel.
Figure 8:
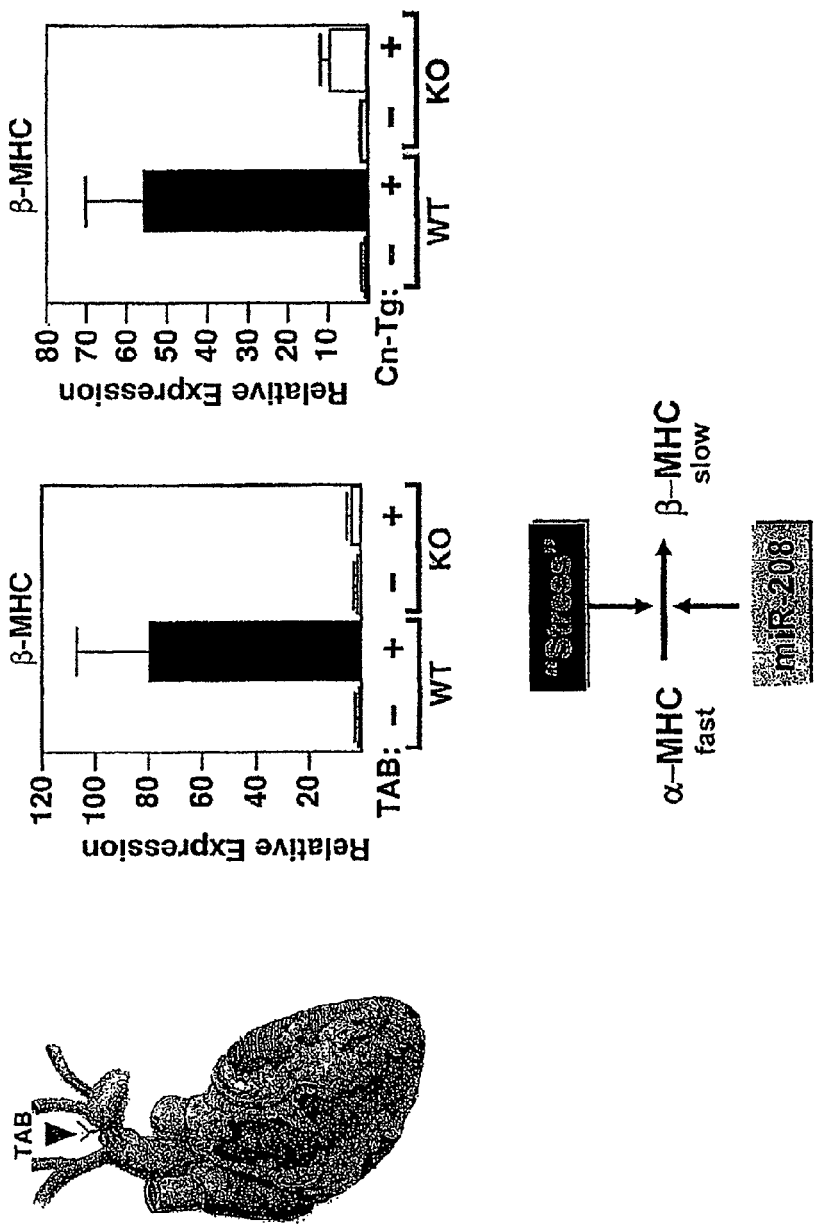
FIG. 8. Mir-208$^{-/-}$ mice fail to up-regulate β-MHC in response to TAB and calcineurin activation.
Figure 9:
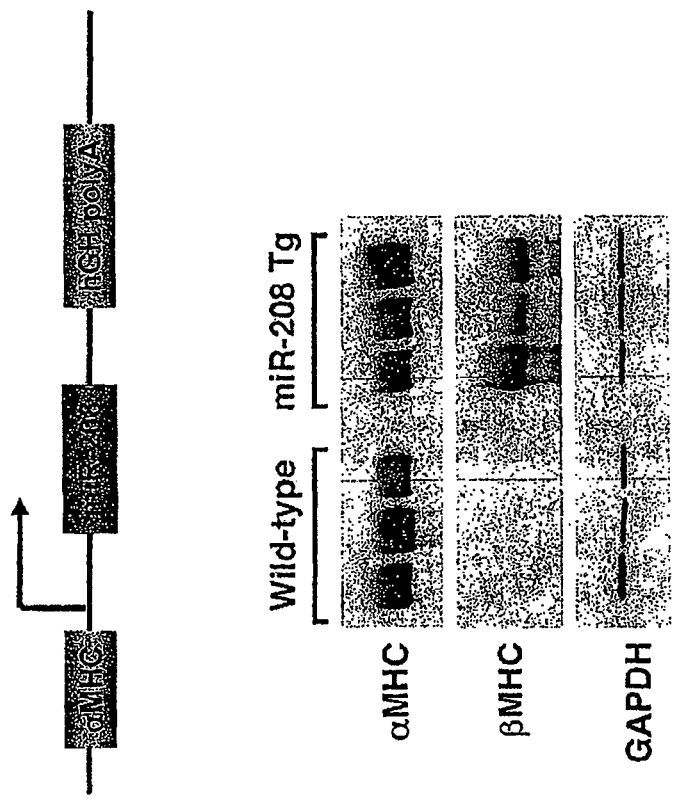
FIG. 9. Western analysis of α and β-MHC protein levels in adult wild-type and miR-208 transgenic animals. GAPDH was detected as a loading control.
Figure 10:
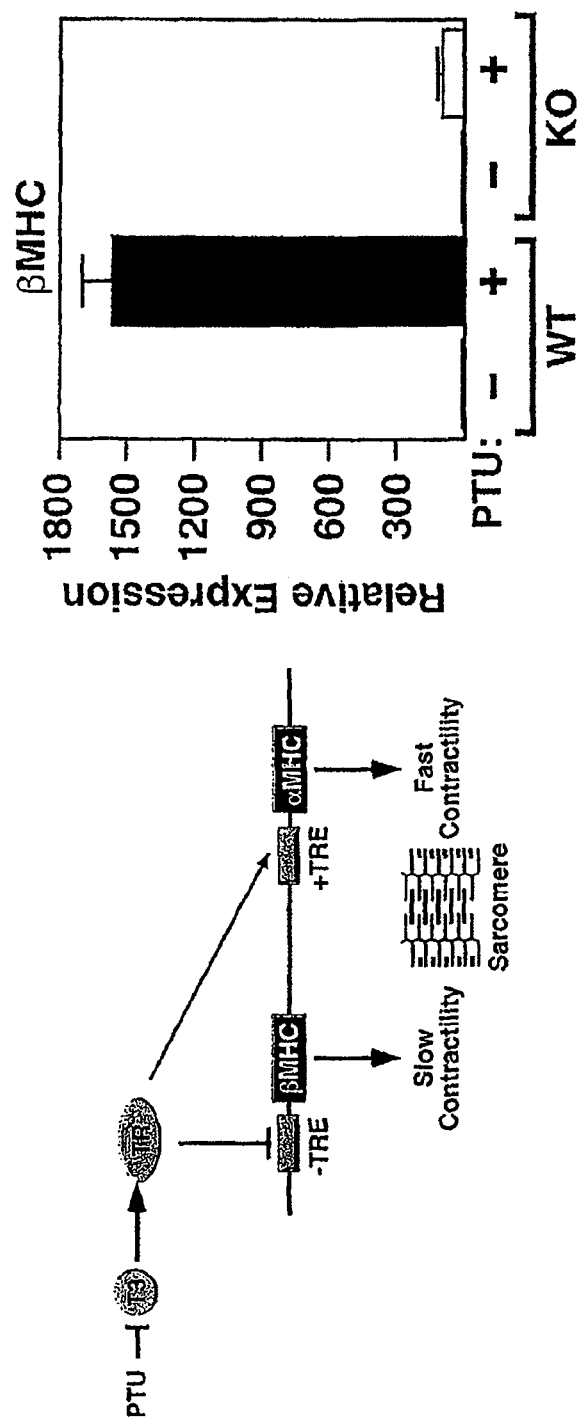
FIG. 10. miR-208$^{-/-}$ mice fail to up-regulate β-MHC in response to hypothyroidism with PTU treatment.
Figure 11:
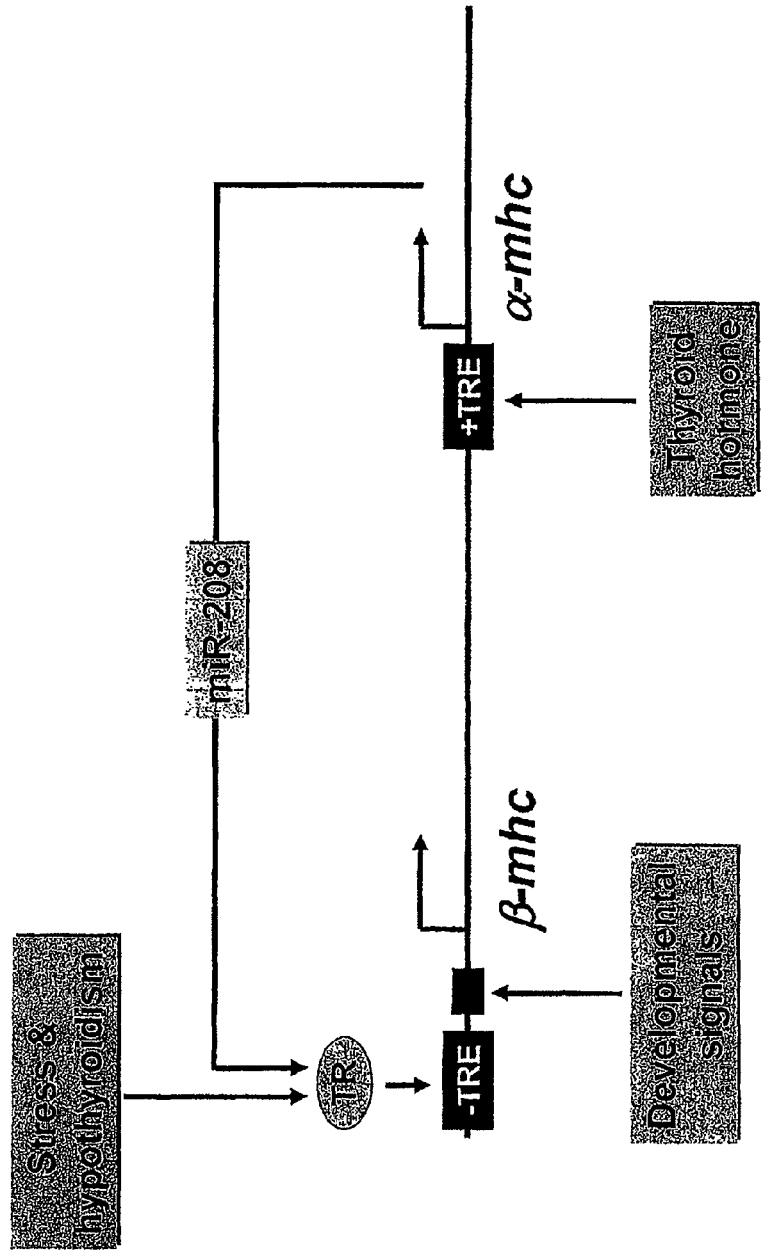
FIG. 11. Schematic diagram of the role of miR-208 in the control of β-MHC expression.

The most remarkable function of miR-208 was revealed by the aberrant response of miR-208-null mice to cardiac stress (van Rooij et al., 2007). In response to pressure overload by thoracic aortic constriction or signaling by calcineurin, a calcium/calmodulin-dependent phosphatase that drives pathological remodeling of the heart, miR-208-null mice showed virtually no hypertrophy of cardiomyocytes or fibrosis and were unable to up-regulate β-MHC expression (FIGS. 6-8). In contrast, other stress responsive genes, such as those encoding ANF and BNP, were strongly induced in miR-208 mutant animals, demonstrating that miR-208 is dedicated specifically to the control of β-MHC expression, which can be uncoupled from other facets of the cardiac stress response.

β-MHC expression is repressed by thyroid hormone signaling and is up-regulated in the hypothyroid state (Leung et al., 2006). miR-208$^{-/-}$ animals were also resistant to up-regulation of β-MHC expression following treatment with the T3 inhibitor propylthiouracil (PTU), which induces hypothyroidism. Intriguingly, however, expression of β-MHC before birth was normal in miR-208 mutant mice, indicating that miR-208 is dedicated specifically to the post-natal regulation of β-MHC expression, which coincides with the acquisition of thyroid hormone responsiveness of the β-MHC gene (FIG. 5).

A clue to the mechanism of action of miR-208 comes from the resemblance of miR-208$^{-/-}$ hearts to hyperthyroid hearts, both of which display a block to β-MHC expression, up-regulation of stress-response genes and protection against pathological hypertrophy and fibrosis (FIGS. 6-10). The up-regulation of fast skeletal muscle genes in miR-208$^{-/-}$ hearts also mimics the induction of fast skeletal muscle fibers in the hyperthyroid state (Wei et al., 2005).

Figure 12:
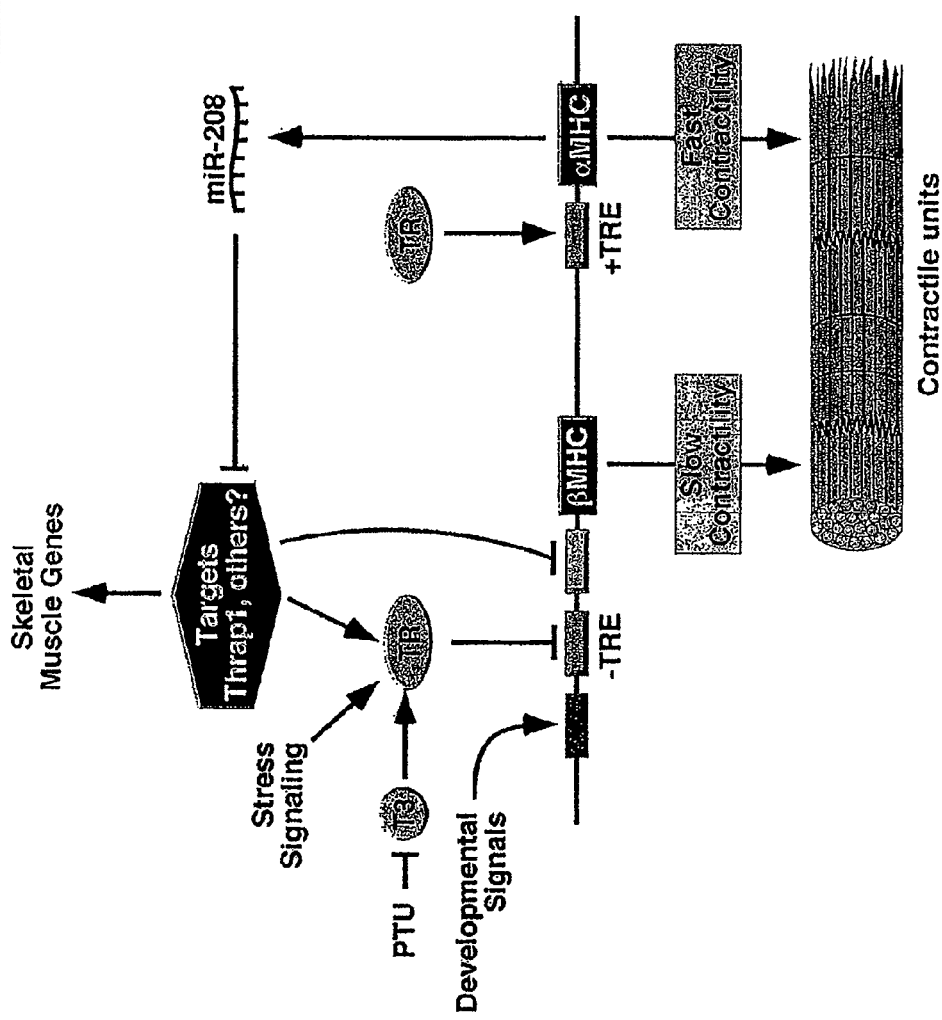
FIG. 12. Schematic diagram of the role of miR-208 in the regulation of β-MHC and fast skeletal muscle gene expression via Thrap1.

These findings suggest that miR-208 acts, at least in part, by repressing expression of a common component of stress-response and thyroid hormone signaling pathways in the heart. Among the strongest predicted targets of miR-208 is the thyroid hormone receptor (TR) co-regulator THRAP1, which can exert positive and negative effects on transcription (Pantos et al., 2006; Yao and Eghbali, 1992; FIG. 12). The TR acts through a negative thyroid hormone response element (TRE) to repress β-MHC expression in the adult heart (Zhao et al., 2005). Thus, the increase in THRAP1 expression in the absence of miR-208 would be predicted to enhance the repressive activity of the TR toward β-MHC expression, consistent with the blockade to β-MHC expression in miR-208−/− hearts. However, although THRAP1 appears to be a bone fide target for miR-208, these data do not exclude the potential involvement of additional targets in the regulation of β-MHC expression.

Figure 13:
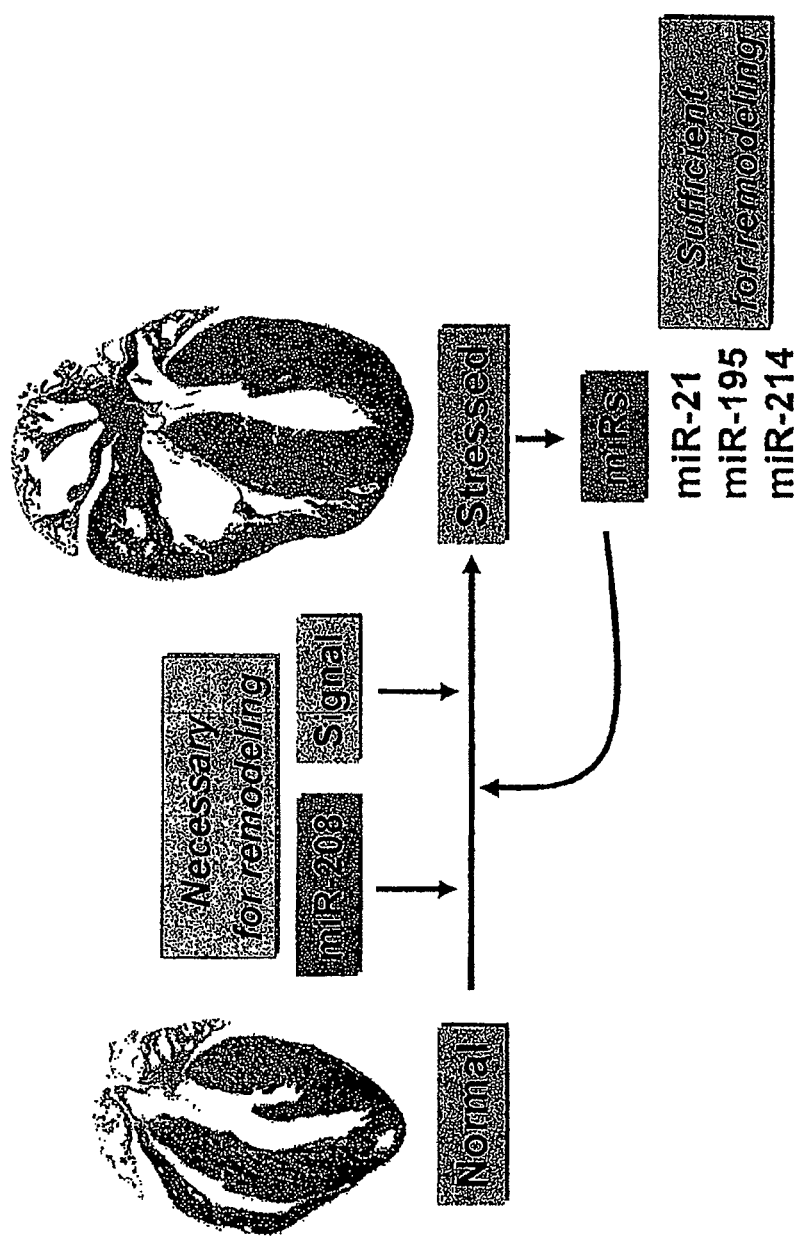
FIG. 13. Mechanisms of action of microRNAs during cardiac hypertrophy.

Since even a subtle shift towards β-MHC reduces mechanical performance and efficiency of the adult heart, it would be of therapeutic value to exploit miR-208 regulation to prevent an increase in β-MHC expression during cardiac disease. The cardiac specificity and dedication of miR-208 to the cardiac stress response, but not to normal cardiac development, make miR-208 (and its down-stream effectors) an attractive therapeutic target for manipulating β-MHC levels (FIG. 13).

Materials and Methods

Northern Blot Analysis.

Cardiac tissue samples of left ventricles of anonymous humans diagnosed as having non-failing or failing hearts were obtained from Gilead Colo. (Westminster, Colo.). Cardiac tissue samples of border zone regions of anonymous humans diagnosed as having suffered a myocardial infarction were obtained. Total RNA was isolated from cells, mouse, rat and human cardiac tissue samples or isolated myocytes by using Trizol reagent (Gibco/BRL). Equal loading was confirmed by staining Northern gels with ethidium bromide. Northern blots to detect microRNAs were performed as described previously (van rooij et al., 2006). A U6 probe served as a loading control. To detect α-MHC expression, a Northern blot containing 10 µg of RNA from cardiac tissue of both adult wild-type and miR-208 mutant animals was probed with a cDNA fragment of α-MHC covering a part of the 5'UTR region and first exon.

PTU Treatment.

Thyroid hormone deficiency was induced by feeding animals for the indicated durations with iodine-free chow supplemented with 0.15% PTU purchased from Harlan Teklad Co. (TD 97061) (Madison, Wis.).

Microarray and Real-Time PCR Analysis.

Total RNA from cardiac tissue was isolated using Trizol (Invitrogen). Microarray analysis was performed using Mouse Genome 430 2.0 array (Affymetrix). To detect the level of miRNA, RT-PCR was performed using the Taqman MicroRNA reverse Transcriptase kit (Applied Biosystems, ABI) according to the manufacturer's recommendations. Five ng of RNA was used to generate cDNA with a miRNA specific primer, after which a miRNA specific Taqman probe served to detect the expression level of the miRNA of interest. Following RT-PCR with random hexamer primers (Invitrogen) on RNA samples, the expression of a subset of genes was analyzed by either PCR or quantitative real time PCR using Taqman probes purchased from ABI.

Generation of miR-208 Mutant Mice.

To generate the miR-208 targeting vector, a 0.4 kb fragment (5' arm) extending upstream of the miR-208 coding region was digested with SacII and NotI and ligated into the pGKneoF2L2dta targeting plasmid upstream of the loxP sites and the Frt-flanked neomycin cassette. A 3.3 kb fragment (3' arm) was digested with SalI and HindIII and ligated into the vector between the neomycin resistance and Dta negative selection cassettes. Targeted ES-cells carrying the disrupted allele were identified by Southern blot analysis with 5' and 3' probes. Three miR-208 targeted ES clones were identified and used for blastocyst injection. The resulting chimeric mice were bred to C57BL/6 to obtain germline transmission of the mutant allele.

Generation of Transgenic Mice.

A mouse genomic fragment flanking the miRNA of interest was subcloned into a cardiac-specific expression plasmid containing the α-MHC and human GH poly(A)+ signal (Kiriazis and Kranias, 2000). Genomic DNA was isolated from mouse tail biopsies and analyzed by PCR using primers specific for the human GH poly(A)+ signal.

Western Blotting.

Myosin was extracted from cardiac tissue as described (Morkin, 2000). MHC isoforms were separated by SDS PAGE and Western blotting was performed with mouse monoclonal α-MHC (BA-G5) (ATCC, Rockville, Md.) and mouse monoclonal antimyosin (slow, skeletal M8421) (Sigma, Mo.), which is highly specific for β-MHC. To detect all striated myosin a pan specific antibody (mouse monoclonal 3-48; Accurate Chemical & Scientific Corporation, NY) was used. THRAP1 was detected by immunoprecipitation from 400 µg of cardiac protein lysate. After pre-clearing the samples for 1 hour at 4° C., the supernatant was incubated overnight at 4° C. with 1 µl rabbit polyclonal anti-THRAP1 (a kind gift of R. Roeder, Rockefeller University) and 15 µl of protein A beads. The beads were washed three times with lysis buffer and boiled in SDS sample buffer. Immunoprecipitated THRAP1 protein was resolved by SDS-PAGE and analyzed using rabbit polyclonal anti-THRAP1 at a dilution of 1:3000 and anti-rabbit IgG conjugated to horseradish peroxidase at a dilution of 1:5000 with detection by Luminol Reagent (Santa Cruz).

Histological Analysis and RNA In Situ Hybridization.

Tissues used for histology were incubated in Krebs-Henselheit solution, fixed in 4% paraformaldehyde, sectioned, and processed for hematoxylin and eosin (H&E) and Masson's Trichrome staining or in situ hybridization by standard techniques (Krenz and Robbins, 2004). $^{35}$S-labeled RNA probes were generated using Maxiscript kit (Amersham). Signals were pseudocolored in red using Adobe Photoshop.

Transthoracic Echocardiography.

Cardiac function and heart dimensions were evaluated by two-dimensional echocardiography in conscious mice using a Vingmed System (GE Vingmed Ultrasound, Horten, Norway) and a 11.5-MHz linear array transducer. M-mode tracings were used to measure anterior and posterior wall thicknesses at end diastole and end systole. Left ventricular (LV) internal diameter (LVID) was measured as the largest anteroposterior diameter in either diastole (LVIDd) or systole (LVIDs). The data were analyzed by a single observer blinded to mouse genotype. LV fractional shortening (FS) was calculated according to the following formula: FS (%)=[(LVIDd−LVIDs)/LVIDd]×100.

Plasmids and Transfection Assays.

A 305 bp genomic fragment encompassing the miR-208 coding region was amplified by PCR and ligated into pCMV6. A 1 kb fragment encompassing the entire murine THRAP1-UTR was PCR-amplified and ligated into an HA-tagged pCMV6 expression construct and the firefly luciferase (f-luc) reporter construct (pMIR-REPORT™, Ambion). A mutation of the UCGUCUUA miR-208 seed binding sequence was constructed through PCR-based mutagenesis.

Cell Culture, Transfection and Luciferase Assays.

A 1793-bp genomic fragment encompassing miR-29b-1 and miR-29a coding region was amplified by PCR and ligated into pCMV6. Genomic fragments of the murine 3'UTR encompassing the miR-29a-c binding site(s) were PCR-amplified and ligated into the firefly luciferase (f-luc) reporter construct (pMIR-REPORT™, Ambion). COS cells were transfected with Fugene 6 (Stratagene) according to manufacturer's instructions. The total amount of DNA per well was kept constant by adding the corresponding amount of expression vector without a cDNA insert. 48 hours after transfection, cell extracts were assayed for luciferase expression using the luciferase assay kit (Promega). Relative promoter activities are expressed as luminescence relative units normalized for β-galactosidase expression in the cell extracts.

Cardiac fibroblasts (CFs) were isolated as described previously (Simpson and Savion, 1982). Briefly, hearts were excised from anesthetized neonatal 1-2 day-old Sprague-Dawley rats (Harlan Sprague Dawley, Indianapolis, Ind.), minced, and digested with pancreatin 0.1%. Cells were plated on primaria plates for 2 h, and the medium which contained the cardiomyocyte fraction of the digested tissue was removed. Cardiac fibroblasts attached and proliferated much more rapidly than cardiac myocytes; this produced virtually pure fibroblast cultures after the first passage, which was confirmed by repeated differential plating and microscopic evaluation. Cells were detached with 0.05% trypsin for passaging, and culture studies were performed at passages 2 to 4. Cells were grown in high glucose (4.5 gm/lt) Dulbecco's modified Eagle's medium (DMEM) containing 10% heat-inactivated FBS and antibiotics (Penicillin and streptomycin). Myofibroblast differentiation was induced by changing the medium to low serum (2% FBS) with L-ascorbic acid (10 µg/µl) and administration of 10 ng/ml TGFβ1 for 48 hours.

In Vivo miR-29b Silencing by Anti-miR Treatment.

Chemically modified antisense oligonucleotides comprosing a sequence complementary to miR-29b (anti-miR-29b) were used to inhibit miR-29b expression. All bases were 2'-OMe modified, the first two and last four bases contained a phosphorothioate internucleoside bond and the 3' end of the oligonucleotides was conjugated to cholesterol. Eight week-old C57BL/6 male mice received either anti-miR-29b (AsAs-CACUGAUUUCAAAUGGUsGsCsUsAs-Cholesterol) or mismatch miR-29b (AsAsAACUGAUGUCACAUGGUsGsAsUsAs-Cholesterol) at a dose of 80 mg/kg body weight or a comparable volume of saline through tail vein injection. Tissues were collected either 3 days or 3 weeks after treatment.

Example 1

Regulation of Cardiac Hypertrophy and Heart Failure by Stress-Responsive miRNAs

Figure 14C:
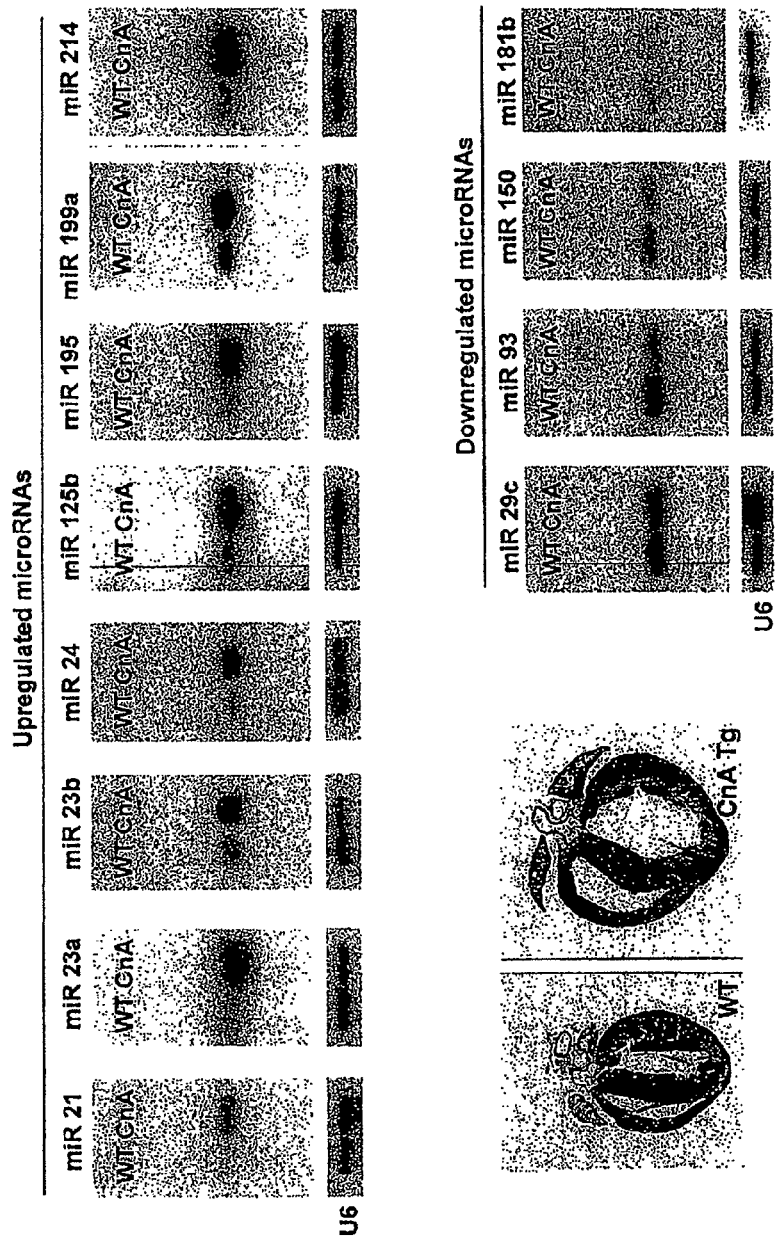

In light of their involvement in modulating cellular phenotypes, the inventors hypothesized that miRNAs may play a role in regulating the response of the heart to cardiac stress, which is known to result in transcriptional and translational changes in gene expression. To investigate the potential involvement of miRNAs in cardiac hypertrophy, they performed a side-by-side miRNA microarray analysis in 2 established mouse models of cardiac hypertrophy, using a microarray that represented 186 different miRNAs (Babak et al., 2004). Mice that were subjected to thoracic aortic banding (TAB), which induces hypertrophy by increased afterload on the heart (Hill et al., 2000), were compared to sham operated animals. In a second model, transgenic mice expressing activated calcineurin (CnA) in the heart, which results in a severe, well-characterized form of hypertrophy (Molkentin et al., 1998), were compared to wild-type littermates (FIG. 14A). RNA isolated from hearts of mice subjected to TAB showed increased expression of 27 miRNAs compared to sham-operated controls, and CnA Tg mice showed increased expression of 33 miRNAs compared with non-transgenic littermate controls, of which 21 were up-regulated in both models. Similarly, TAB and CnA-induced hypertrophy were accompanied by reduced expression of 15 and 14 miRNAs, respectively, of which 7 miRNAs were down-regulated in common (FIG. 14B). Northern analysis of these miRNAs (unpublished data) and previous microarray analyses (Barad et al., 2004; Sempere et al., 2004; Shingara et al., 2005; Liu et al., 2004) indicate that they are expressed in a wide range of tissues. Based on their relative expression levels, conservation of human, rat and mouse sequences, and levels of expression during hypertrophy, the inventors focused on 11 up- and 5 down-regulated miRNAs (FIG. 14C).

Northern blot analysis of cardiac RNA from WT and CnA Tg animals confirmed an increased expression of miRs-21, -23, -24, -125b, -195, -199a, and -214, and decreased expression of miRs-29, -93, -150 and -181b (FIG. 14C and FIG. 15). Collectively, these data indicate that distinct miRNAs are regulated during cardiac hypertrophy, suggesting the possibility that they function as modulators of this process.

Example 2

Discovery of the miR-29 Family as Down-Stream Targets for Regulation by miR-208

Figure 16:
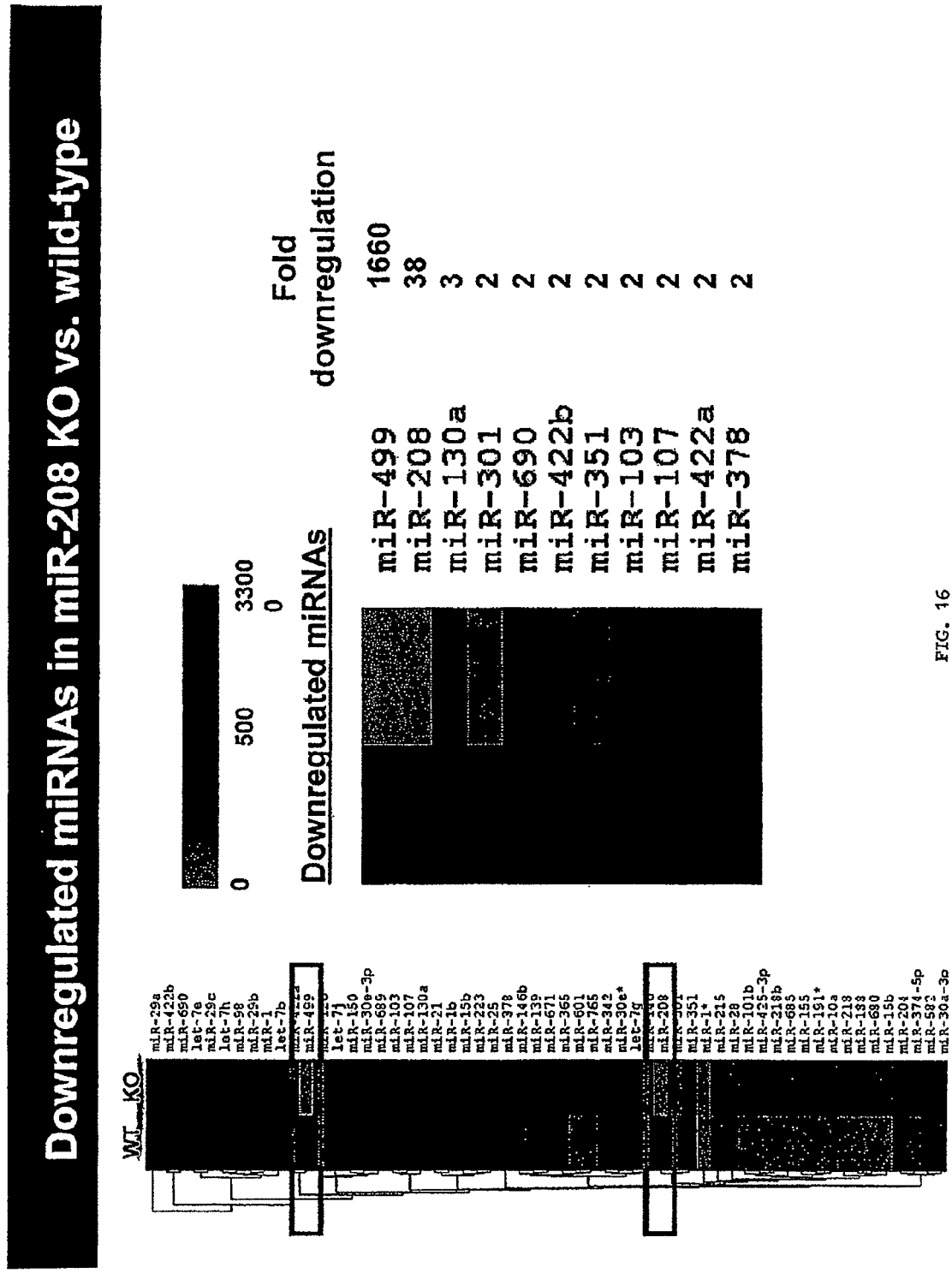
FIG. 16. Microarray analysis of hearts from miR-208 knockout mice compared to wild-type. Microarray analysis was performed on mRNA isolated from wild-type and miR-208-null hearts at 6 weeks of age. The most down-regulated miRNA, next to miR-208, is miR-499.
Figure 17:
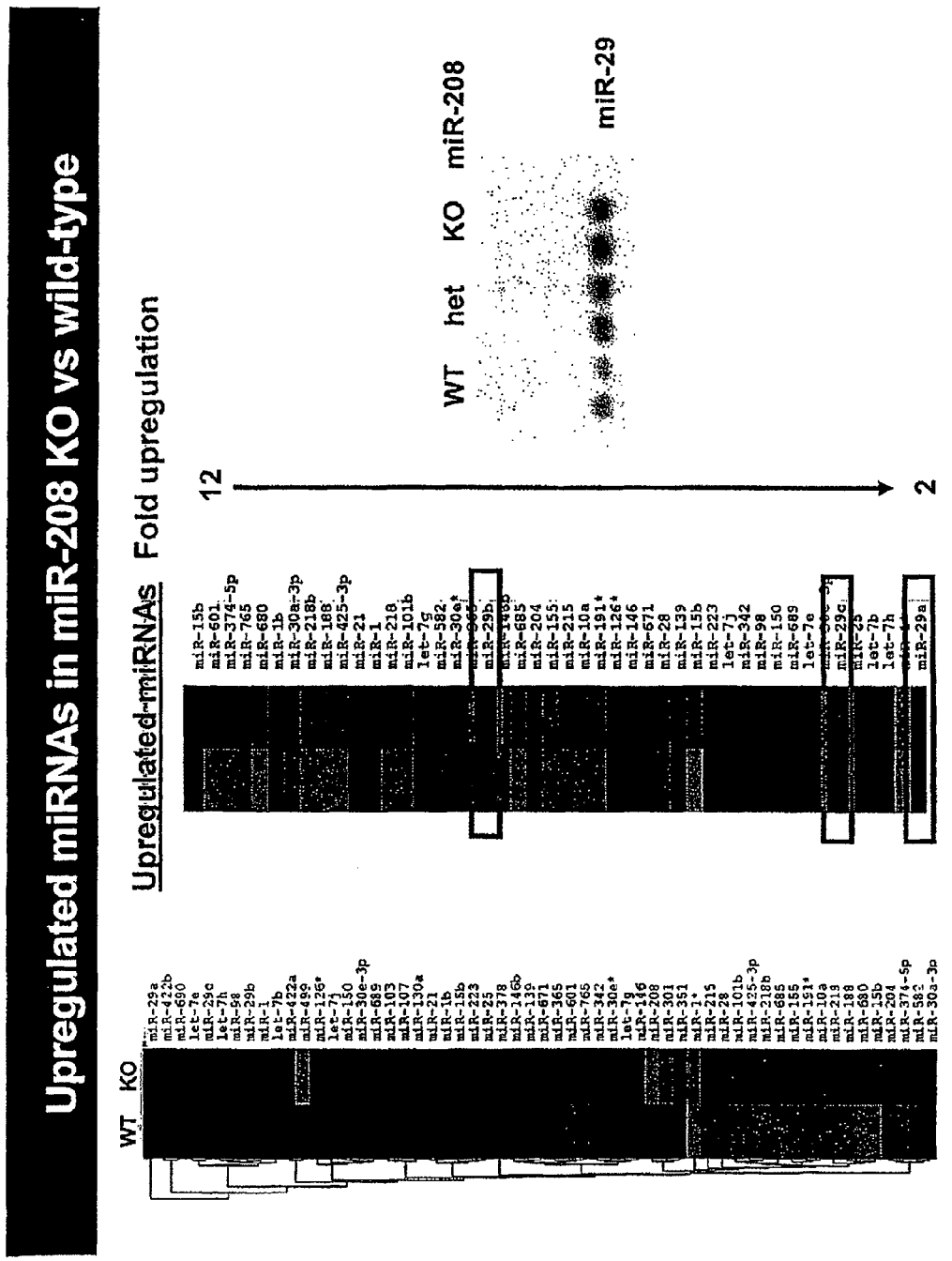
FIG. 17. miR-29 family is dramatically up-regulated in miR-208-null hearts.
Figure 18:
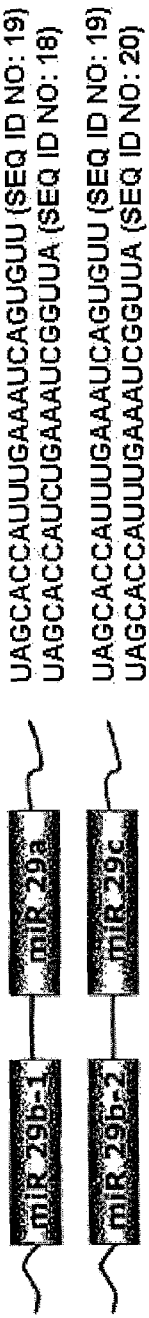
FIG. 18. miR-29 family targets mRNAs encoding collagens and other components of the extracellular matrix involved in fibrosis. Based on their high sequence homology, the miR 29 family consists of 4 members; miR-29a, miR29b-1 and -2 and miR-29c. The sequences of the mature miRNAs are shown (SEQ ID NOS:18-20). The mature sequences of miR-29b-1 and miR-29b-2 are identical. Together this family is directed against many components of the extracellular matrix involved in fibrosis.
Figure 19:
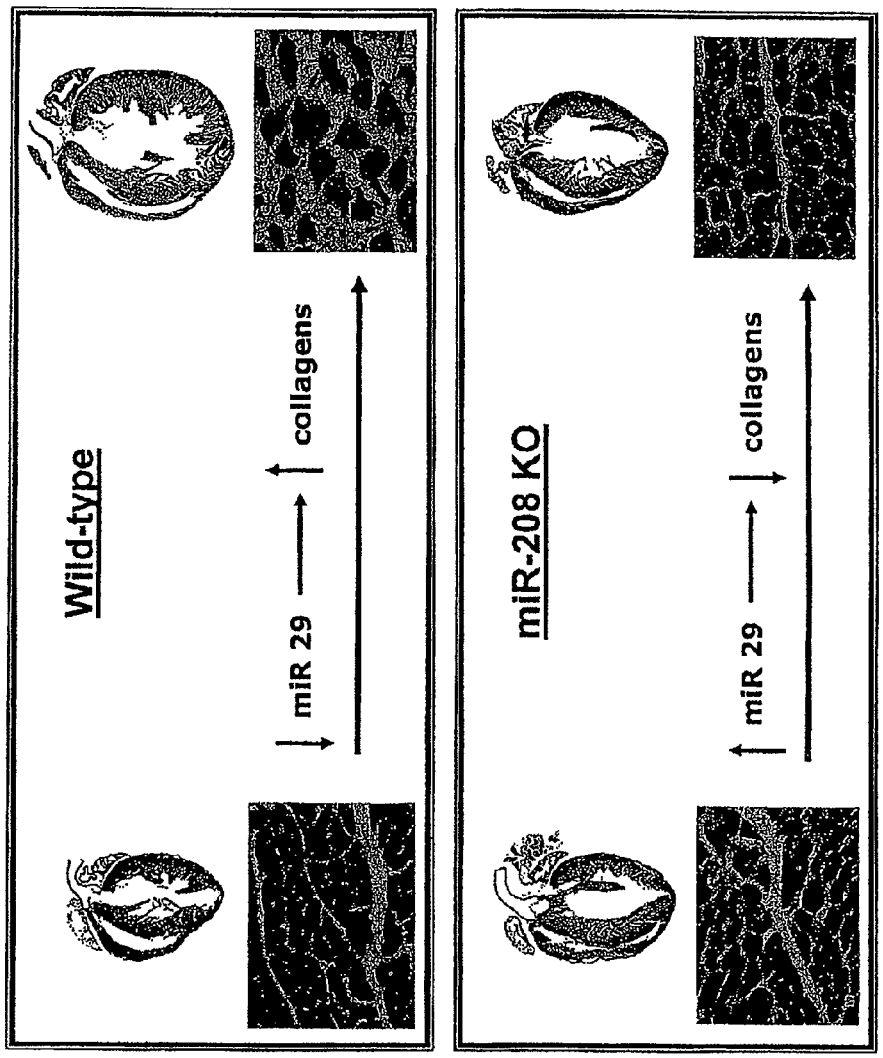
FIG. 19. Model for the control of cardiac fibrosis by miR-208 and miR-29 family. In the normal heart, miR-208 inhibits the expression of miR-29a-c. In the absence of miR-208, miR-29a-c expression is up-regulated, preventing the expression of extracellular matrix and fibrosis in response to stress. The functions of miR-208, miR-499 and miR-29 are interlinked. Loss of miR-208 can be cardioprotective by preventing expression of miR-499 and up-regulating expression of miR-29a-c, with consequent blockade to fibrosis.

The inventors performed a miRNA microarray on hearts from wild-type and miR-208-null mice in an effort to identify downstream miRNAs that might mediate the actions of miR-208 (FIG. 16). They discovered that multiple members of the miR-29 family were up-regulated in miR-208-null mice (FIG. 17). Target prediction indicated that miR-29 family members targeted mRNAs encoding multiple collagens and other components of the extracellular matrix (FIG. 18). Thus, the up-regulation of miR-29 family members in miR-208-null mice is likely to account for the block to fibrosis seen in these animals (FIG. 19).

The discovery that miR-29a-c is down-regulated in the diseased heart and targets mRNAs encoding collagens and extracellular matrix proteins suggests that strategies to enhance expression of miR-29a-c or its association with target mRNAs can have beneficial effects on the heart in the settings of pathological cardiac remodeling and fibrosis. Moreover, elevation of miR-29a-c expression or function may prevent fibrosis associated with many diseases in tissues such as skeletal muscle, liver, lung, kidney and others. In addition, the discovery that miR-208 represses miR-29a-c expression, and that loss of miR-208 upregulates miR-29a-c expression, indicates that miR-29a-c is a downstream mediator of the actions of miR-208 on the heart.

Example 3

MiR-29a-c Regulates the Expression of Fibrotic Genes

To begin to define the possible functions for miR-29a-c in the heart following MI, the inventors made use of computational predictions to identify possible miR-29a-c targets. The Targetscan prediction website indicated an unexpectedly high number of fibrosis-related mRNAs encoding collagens, metallopeptidases, and integrins as possible targets for miR-29a-c (word-wide web at targetscan.org). To determine whether the downregulation of miR-29a-c might regulate cardiac fibrosis, the inventors focused on predicted targets implicated in ECM production in heart. Elastin (ELN), fibrillin 1 (FBN1), collagen type I, α1 and α2 (COL1A1, COL1A2) and collagen type III, α1 (COL3A1) all contain one or more conserved potential seed sequences for miR-29a-c (FIG. 20A).

Because miRNAs down-regulate the steady state levels, as well as the translation, of their target mRNAs, the inventors analyzed the expression of predicted miR-29a-c mRNA targets. Real-time RT-PCR analysis of these key regulatory genes for cardiac fibrosis in cardiac samples 3 days after MI indicated that the specific downregulation of miR-29a-c in the infarcted region correlates with the increase in expression of COL1A1, COL1A2, COL3A1, and FBN1. In contrast, ELN appeared unchanged in the border zone, and even showed an increase in the remote myocardium (FIG. 20B).

Using a CMV-driven expression plasmid, the inventors overexpressed miR-29b-1 and miR-29a in COS cells (FIG. 20C) with luciferase expression plasmids containing the 3'-UTRs of the predicted miR-29a-c targets. Increasing amounts of CMV-driven miR-29b-1/miR-29a resulted in a dose-dependent decrease in luciferase activity, while comparable amounts of miR-206, as a control, had no effect (FIGS. 20C-D), substantiating these mRNAs as targets for repression by miR-29a-c.

Example 4

Regulation of miR-29a-c in Cardiac Fibroblasts

Cardiac fibrosis is a major aspect of the remodeling process typically seen in the failing heart. The proliferation of fibroblasts and increased deposition of ECM components results in myocardial stiffness and diastolic dysfunction. Transforming growth factor β (TGFβ) has been shown to play a dominant role in the production and deposition of collagens in the heart and induces a transformation of fibroblasts into myofibroblasts (Border and Noble, 1994). Real-time PCR analysis on cardiac fibroblasts exposed to TGFβ revealed a decrease in miR-29a-c expression, suggesting that the decrease in miR-29a-c following MI might be TGFβ-regulated (FIG. 21A). Interestingly, natriuretic peptides like B-type natriuretic peptide (BNP) have been shown to inhibit TGFβ-regulated gene expression related to fibrosis and myofibroblast conversion (Kapoun et al., 2004). In this regard, the inventors reported previously that mice lacking the cardiac-specific miRNA miR-208 were resistant to cardiac fibrosis and remodeling and exhibited increased expression of BNP at baseline (van Rooij et al., 2007). Since BNP is known to antagonize the effects of TGFβ, the inventors speculated that the increased levels of BNP in these mice might enhance the expression of miR-29a-c. Indeed, Northern analysis showed a dose-dependent increase in miR-29a-c expression upon removal of miR-208, which coincided with an increasing expression level of BNP (FIG. 21B). These data indicate that TGFβ induces the expression of collagen related genes in fibroblasts at least partly through decreasing the level of miR-29a-c, which can be inhibited by BNP secreted by cardiomyocytes.

Example 5

In Vivo Knockdown of miR-29a-c Induces Fibrosis and Expression of Collagen Genes To further explore the potential role of miR-29a-c as a negative regulator of collagen expression, the inventors knocked down miR-29b in vivo using cholesterol-modified oligonucleotides complementary to the mature miRNA sequence of miR-29b (anti-miR-29b) and either saline or an oligonucleotide containing a four-base mismatch (mm miR-29b) as a negative control (FIG. 22A). Three days after a single tail vein injection of anti-miR-29b (80 mg/kg), the inventors observed a dramatic diminution of miR-29b expression in all tissues examined (FIG. 22B). In contrast, a comparable dose of the mm miR-29b antisense oligonucleotide had no effect on the expression level of miR-29b compared to the saline control. Knockdown by anti-miR-29b appeared to be specific to the mature miRNA, since the level of pre-miRNA remained comparable between anti-miR and mm treated animals. While the knockdown in the liver and kidney appeared to be complete, a low level of miR-29b remained detectable in the heart and lung (FIG. 22B).

Figure 23:
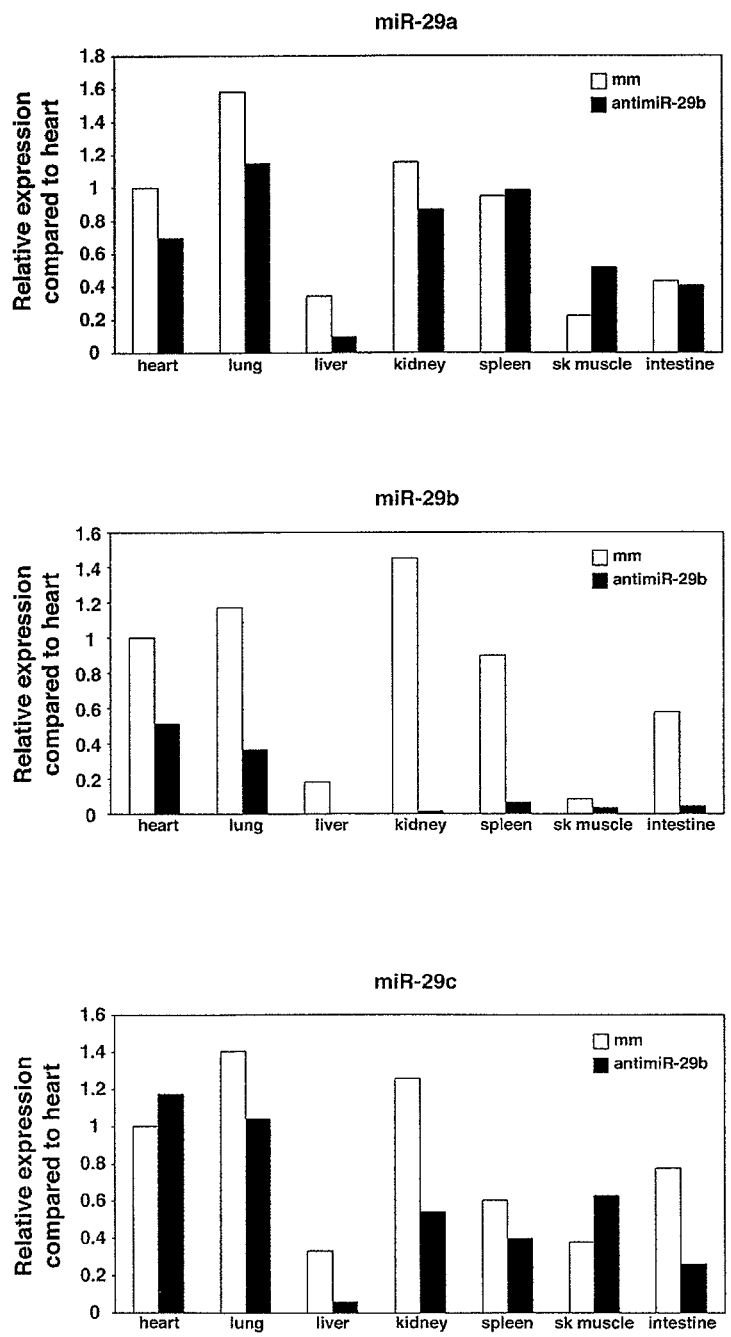
FIG. 23. Expression of miR-29 family members in various tissues in response to miR-29b knockdown. Knockdown of all miR-29 members in the different tissues indicates that miR-29b shows a 50% reduction in the heart in response to anti-miR-29b, while miR-29a and -c only show marginal changes. However, the knockdown of miR-29b in liver and kidney in response to anti-miR-29b is almost complete, while miR-29a and -c also appear to be reduced in these tissues in response to anti-miR-29b.

Since the other miR-29 members share high sequence homology with miR-29b, the expression of miR-29a and -c in response to anti-miR-29b was also examined. While a significant knockdown in liver and kidney (especially for miR-29c), was detected, cardiac expression did not appear to change (FIG. 23). Real-time PCR analysis indicated that miR-29b knockdown was sufficient to induce the expression of collagen genes in the liver specifically, while this effect was absent in the mismatch controls (FIG. 22C).

To enhance cardiac knockdown of miR-29b, the inventors injected 80 mg/kg of oligonucleotide intravenously on two consecutive days and collected material 3 weeks later. Northern analysis indicated complete knockdown of miR-29b in kidney and liver in response to anti-miR-29b compared to the expression level seen after mm miR-29b injection. Cardiac levels of miR-29b were also dramatically reduced, while the expression of miR-29b in lung appeared unaffected by anti-miR-29b (FIG. 22D). Collagen expression in the heart was increased in response to miR-29b inhibition (FIG. 22E). Taken together, these data indicate that miR-29b functions as a negative regulator of collagen gene expression in vivo and thereby influences collagen deposition and fibrosis in the heart and liver.

Example 6

Down-Regulation of Collagen Expression with a miR-29a-c Mimic

To determine whether overexpression of miR-29a-c was capable of reducing collagen expression, the inventors exposed fibroblasts to a miR-29b mimic. The level of miR-29b expression in fibroblasts cultures increased by as much as 400-fold after 3 days of exposure to miR-29b mimic (FIG. 22F). miR-29a expression was unaffected and miR-29c expression was increased only slightly by miR-29b mimic (FIG. 22F). Real-time PCR analysis indicated that the expression of collagen genes was diminished in response to miR-29b mimic (FIG. 22G). However, the magnitude of the decrease in collagen expression was modest compared to the increase in expression of miR-29b, indicating that miR-29a-c levels are not the sole determinant of collagen levels.

All publications, patents and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,873,191
U.S. Pat. No. 5,604,251
U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Publn. 20020150626
U.S. Publn. 20030032615
U.S. Publn. 20030203865
U.S. Publn. 20040048787
Abraham et al., *Mol. Med.*, 8:750-760, 2002.
Ambros, *Cell*, 113(6):673-676, 2003.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Babak et al., *RNA* 10:1813-1819, 2004.
Baichwal and Sugden, In: *Gene Transfer*, Kucherlapati (Ed.), Plenum Press, NY, 117-148, 1986.
Banerji et al., *Cell*, 27(2 Pt 1):299-308, 1981.
Banerji et al., *Cell*, 33(3):729-740, 1983.
Barad et al., *Genome Res.* 14:2486-2494, 1997.
Barnes et al., *J. Biol. Chem.*, 272(17):11510-11517, 1997.
Bartel, *Cell*, 116:281-297, 2004.
Benvenisty and Neshif, *Proc. Natl. Acad. Sci. USA*, 83(24):9551-9555, 1986.
Berk et al., *J. Clin. Invest.* 117:568-575, 2007.
Berkhout et al., *Cell*, 59:273-282, 1989.
Bhaysar et al., *Genomics*, 35(1):11-23, 1996.
Blanar et al., *EMBO J.*, 8:1139, 1989.
Bodine and Ley, *EMBO J.*, 6:2997, 1987.
Border and Noble, *N. Engl. J. Med.*, 331:1286-1292, 1994.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82(13):4438-4442, 1985.
Bristow, *Cardiology*, 92:3-6, 1999.
Bulla and Siddiqui, *J. Virol.*, 62:1437, 1986.
Calin et al., *Proc. Natl. Acad. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Care et al., *Nat. Med.* 13:613-618, 2007.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Mol. Cell. Biol.*, 9:2153, 1989.
Chang et al., *Nature*, 430(7001):785-789, 2004.
Chatterjee et al., *Proc. Natl. Acad. Sci. USA*, 86:9114, 1989.
Chen and Okayama, *Mol. Cell. Biol.*, 7(8):2745-2752, 1987.
Chen et al., *Science*, 303(5654):83-86, 2004.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Durand et al., *Ann. Med.*, 27:311-317, 1995.
Edbrooke et al., *Mol. Cell. Biol.*, 9:1908, 1989.
Edgerton and Roy, *J. Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fatkin et al., *J. Clin. Invest.*, 106(11):1351-1359, 2000.
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Franz et al., *Cardioscience*, 5(4):235-43, 1994.
Frey et al., *Circulation* 109:1580-1589, 2004.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Gopal-Srivastava et al., *J. Mol. Cell. Biol.* 15(12):7081-7090, 1995.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.

Heineke and Molkentin, *Nat. Rev. Mol. Cell. Biol.* 7:589-600, 2006.
Hen et al., *Nature,* 321:249, 1986.
Hensel et al., *Lymphokine Res.,* 8:347, 1989.
Hermonat and Muzycska, *Proc. Natl. Acad. Sci. USA,* 81:6466-6470, 1984.
Herr and Clarke, *Cell,* 45:461, 1986.
Hersdorffer et al., *DNA Cell Biol.,* 9:713-723, 1990.
Herz and Gerard, *Proc. Natl. Acad. Sci. USA,* 90:2812-2816, 1993.
Hill et al., *Circulation,* 101:2863-2869, 2000.
Hirochika et al., *J. Virol.,* 61:2599, 1987.
Hirsch et al., *Mol. Cell. Biol.,* 10:1959, 1990.
Holbrook et al., *Virology,* 157:211, 1987.
Horlick and Benfield, *Mol. Cell. Biol.,* 9:2396, 1989.
Horwich et al. *J. Virol.,* 64:642-650, 1990.
Huang et al., *Cell,* 27:245, 1981.
Hug et al., *Mol. Cell. Biol.,* 8:3065, 1988.
Hutvagner et al., *PLoS Biol.,* 2(4):E98, 2004.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Ito and Roeder, *Trends Endocrinol. Metab.,* 12:127-134, 2001.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Mol. Cell. Biol.,* 9:3393, 1989.
Jones and Shenk, *Cell,* 13:181-188, 1978.
Kadesch and Berg, *Mol. Cell. Biol.,* 6:2593, 1986.
Kaneda et al., *Science,* 243:375-378, 1989.
Kapoun et al., *Circ. Res.,* 94:453-461, 2004.
Karin et al., *Mol. Cell. Biol.,* 7:606, 1987.
Karin et al., *Mol. Cell. Biol.,* 7:606, 1987.
Karlsson et al., *EMBO J.,* 5:2377-2385, 1986.
Katinka et al., *Cell,* 20:393, 1980.
Katinka et al., *Nature,* 290:720, 1981.
Kato et al, *J. Biol. Chem.,* 266:3361-3364, 1991.
Kawamoto et al., *Mol. Cell. Biol.,* 8:267, 1988.
Kelly et al., *J. Cell Biol.,* 129(2):383-396, 1995.
Kiledjian et al., *Mol. Cell. Biol.,* 8:145, 1988.
Kimura et al., *Dev. Growth Differ.* 39(3):257-265, 1997.
Kinugawa et al., *Circ. Res.,* 89:591-598, 2001.
Kinugawa et al., *J. Clin. Endocrinol. Metab.,* 86:5089-5090, 2001.
Kiriazis and Kranias, *Annu. Rev. Physiol.,* 62:321-351, 2000.
Klaassen's The Pharmacological Basis of Therapeutics
Klamut et al., *Mol. Cell. Biol.,* 10:193, 1990.
Klein et al., *Nature,* 327:70-73, 1987.
Koch et al., *Mol. Cell. Biol.,* 9:303, 1989.
Krek et al., *Nature Genetics,* 37:495-500, 2005.
Krenz and Robbins, *J. Am. Coll. Cardiol.,* 44:2390-2397, 2004.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983a.
Kriegler et al., *Cell,* 38:483, 1984.
Kriegler et al., *Cell,* 53:45, 1988.
Kriegler et al., In: *Gene Expression,* Alan Liss (Ed.), Hamer and Rosenberg, New York, 1983b.
Kriitzfeldt et al., *Nature,* 438:685-689, 2005.
Kuhl et al., *Cell,* 50:1057, 1987.
Kunz et al., *Nucl. Acids Res.,* 17:1121, 1989.
Lagos-Quintana et al., *Science,* 294(5543):853-858, 2001.
LaPointe et al., *Hypertension* 27(3 Pt 2):715-22, 1996.
LaPointe et al., *J. Biol. Chem.,* 263(19):9075-8, 1988.
Larsen et al., *Proc Natl. Acad. Sci. USA.,* 83:8283, 1986.
Laspia et al., *Cell,* 59:283, 1989.
Latimer et al., *Mol. Cell. Biol.,* 10:760, 1990.
Lau et al., *Science,* 294(5543):858-862, 2001.
Le Gal La Salle et al., *Science,* 259:988-990, 1993.
Lee and Ambros, *Science,* 294(5543):862-864, 2001.
Lee et al., *Nature,* 294:228, 1981.
Leung et al., *Proc. Natl. Acad. Sci. USA,* 48:18125-18130, 2006.
Levinson et al., *Nature,* 295:79, 1982.
Levrero et al., *Gene,* 101:195-202, 1991.
Lin et al., *Mol. Cell. Biol.,* 10:850, 1990.
Liu et al., *Proc Natl Acad Sci USA* 101:9740-9744, 2004.
Lowes et al., *J. Clin. Invest.,* 100(9):2315-2324, 1997.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.
Majors and Varmus, *Proc. Natl. Acad. Sci. USA,* 80:5866, 1983.
Mann et al., *Cell,* 33:153-159, 1983.
Markowitz et al., *J. Virol.,* 62:1120-1124, 1988.
McKinsey and Olson, *J. Clin. Invest.,* 115(3):538-546, 2005.
McNeall et al., *Gene,* 76:81, 1989.
Meister and Tuschl, *Nature,* 431:343-9, 2004.
Miksicek et al., *Cell,* 46:203, 1986.
Miyata et al., *Circ. Res.,* 86(4):386-390, 2000.
Molkentin et al., *Cell* 93:215-228, 1998.
Mordacq and Linzer, *Genes and Dev.,* 3:760, 1989.
Moreau et al., *Nucl. Acids Res.,* 9:6047, 1981.
Morkin, *Microsc. Res. Tech.,* 50:522-531, 2000.
Moss et al., *Biol. Chem.,* 271(49):31688-31694, 1996.
Muesing et al., *Cell,* 48:691, 1987.
Nakao et al., *Clin. Invest.,* 100(9):2362-2370, 1997.
Ng et al., *Nuc. Acids Res.,* 17:601, 1989.
Nicolas and Rubinstein, In: *Vectors: A survey of molecular cloning vectors and their uses,* Rodriguez and Denhardt (Eds), Stoneham: Butterworth, 494-513, 1988.
Nicolau and Sene, *Biochim. Biophys. Acta,* 721:185-190, 1982.
Nicolau et al., *Methods Enzymol.,* 149:157-176, 1987.
Ondek et al., *EMBO J.,* 6:1017, 1987.
Ornitz et al., *Mol. Cell. Biol.,* 7:3466, 1987.
Palmiter et al., *Nature,* 300:611, 1982.
Pantos et al., *Horm. Metab. Res.,* 38:308-313, 2006.
Paskind et al., *Virology,* 67:242-248, 1975.
Pasquinelli and Ruvkun, *Ann. Rev. Cell Dev. Biol.,* 18:495-513, 2002.
PCT Appln. WO 0071096
PCT Appln. WO 84/03564
PCT Appln. WO 98/33791
Pech et al., *Mol. Cell. Biol.,* 9:396, 1989.
Pelletier and Sonenberg, *Nature,* 334(6180):320-325, 1988.
Perales et al., *Proc. Natl. Acad. Sci. USA,* 91:4086-4090, 1994.
Perez-Stable and Constantini, *Mol. Cell. Biol.,* 10:1116, 1990.
Physicians Desk Reference
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.

Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2:1144, 1988.
Sambrook and Russell, Molecular Cloning: A Laboratory Manual 3rd Ed., Cold Spring Harbor Laboratory Press, 2001.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sempere et al., *Genome Biol* 5:R13, 2004.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shingara et al., *RNA* 11:1461-1470, 2005.
Simpson and Savion, *Circ. Res.*, 50:101-116, 1982.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J. Virology*, 62:614, 1988.
Top et al., *J. Infect. Dis.*, 124:155-160, 1971.
Treisman, *Cell*, 46(4):567-174, 1986
Tronche et al., *Mol. Biol. Med.*, 7:173, 1990.
Tronche et al., *Mol. Cell. Biol.*, 9(11):4759-4766, 1989.
Trudel and Constantini, *Genes and Dev.*, 6:954, 1987.
Tur-Kaspa et al., *Mol. Cell. Biol.*, 6:716-718, 1986.
Tyndell et al., *Nuc. Acids. Res.*, 9:6231, 1981.
van Rooij et al., *Proc. Natl. Acad. Sci. USA*, 103(48):18255-18260, 2006.
van Rooij et al., *Science* 316(5824):575-579. 2007
Vannice and Levinson, *J. Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Wei et al., *J. Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Xu et al., *Curr. Biol.*, 13:790-795, 2003.
Yamauchi-Takihara et. al., *Proc. Natl. Acad. Sci. USA*, 86(10):3504-3508, 1989.
Yang and Russell, *Proc. Natl. Acad. Sci. USA*, 87:4144-4148, 1990.
Yang et al., *Nat. Med.* 13:486-491, 2007.
Yao and Eghbali, *Circ. Res.* 71:831-839, 1992.
Young et al., In: *Handbook of Applied Therapeutics*, 7.1-7.12 and 9.1-9.10, 1989.
Yu et al., *Biochem. Biophys. Res. Commun.* 349(1):59-68. Epub Aug. 11, 2006.
Yutzey et al. *Mol. Cell. Biol.*, 9:1397, 1989.
Zelenin et al., *FEBS Lett.*, 287(1-2):118-120, 1991.
Zeng et al., *Mol. Cell.*, 9(6):1327-33, 2002.
Zhao et al., *Proc. Natl. Acad. Sci. USA*, 102(13):4890-4895, 2005.
Ziober and Kramer, *J. Bio. Chem.*, 271(37):22915-22, 1996

The invention claimed is:

1. A method of increasing expression of one or more extracellular matrix genes in a subject in need thereof comprising administering to the fibroblast cells of the subject an antisense oligonucleotide comprising a sequence that is at least partially complementary to a miR-29a, miR-29b, and/or miR-29c sequence, wherein the expression of one or more extracellular matrix genes in the fibroblast cells of the subject is increased following administration of the antisense oligonucleotide.

2. The method of claim 1, wherein one or more extracellular matrix genes is elastin (ELN), fibrillin 1 (FBN1), collagen type I α1 (COL1A1), collagen type I α2 (COL1A2), collagen type III α1 (COL3A1), collagen type IV α4 (COL4A4), collagen type V α3 (COL5A3), collagen type XI α1 (COL11A1), collagen type V α1 (COL5A1), or collagen type IV α5 (COL4A5).

3. The method of claim 1, wherein the antisense oligonucleotide comprises a sequence that is at least partially complementary to SEQ ID NO: 18, SEQ ID NO: 19, and/or SEQ ID NO: 20.

4. The method of claim 3, wherein the antisense oligonucleotide comprises a sequence that is at least 85% complementary to SEQ ID NO: 18, SEQ ID NO: 19, and/or SEQ ID NO: 20.

5. The method of claim 3, wherein the antisense oligonucleotide comprises a sequence that is at least 95% complementary to SEQ ID NO: 18, SEQ ID NO: 19, and/or SEQ ID NO: 20.

6. The method of claim 3, wherein the antisense oligonucleotide comprises a sequence that is 100% complementary to SEQ ID NO: 18, SEQ ID NO: 19, and/or SEQ ID NO: 20.

7. The method of claim 1, wherein the antisense oligonucleotide comprises a sequence that is substantially complementary to a pre-miR-29a, pre-miR-29b, or pre-miR-29c sequence.

8. The method of claim 1, wherein the antisense oligonucleotide is about 15 to about 50 nucleotides in length.

9. The method of claim 1, wherein the antisense oligonucleotide is about 19 to about 25 nucleotides in length.

10. The method of claim 1, wherein the antisense oligonucleotide comprises at least one sugar and/or backbone modification.

11. The method of claim 10, wherein the sugar modification is a modification selected from the group consisting of 2'-O-alkyl, 2'-O-methyl, 2'-O-methoxyethyl, 2'-fluoro, and a locked nucleic acid.

12. The method of claim 10, wherein the backbone modification is a phosphorothioate linkage.

13. The method of claim 1, wherein the antisense oligonucleotide is conjugated to cholesterol at its 3' terminus.

14. The method of claim 1, wherein the antisense oligonucleotide is administered by oral, intradermal, intramuscular, intravenous, subcutaneous, topical, or intraperitoneal administration.

15. The method of claim 1, wherein the subject has damaged skin tissue.

16. The method of claim 15, wherein the damaged skin tissue comprises a wound, a scar, wrinkles, stretch marks, sun damage, chemical damage, heat damage, or cold damage.

* * * * *